United States Patent [19]

Adamczyk et al.

[11] Patent Number: 5,407,835
[45] Date of Patent: Apr. 18, 1995

[54] REAGENTS AND METHODS FOR THE QUANTIFICATION OF AMITRIPTYLINE OR NORTRIPTYLINE IN BIOLOGICAL FLUIDS

[75] Inventors: Maciej Adamczyk, Gurnee; Jeffrey R. Fishpaugh, Chicago; Donald Johnson, Lindenhurst; Daryl E. Hartter, Mundelein, all of Ill.

[73] Assignee: Abbott Laboratories, Abbott Park, Ill.

[21] Appl. No.: 916,067

[22] Filed: Jul. 24, 1992

Related U.S. Application Data

[63] Continuation-in-part of Ser. No. 738,635, Jul. 31, 1991, abandoned.

[51] Int. Cl.$^6$ ............... G01N 33/542; G01N 33/533; G01N 33/535
[52] U.S. Cl. .................... 436/537; 435/7.93; 436/544; 436/546; 436/815
[58] Field of Search ............... 435/7.9, 7.93; 436/536, 436/537, 544, 545, 546, 815

[56] References Cited

U.S. PATENT DOCUMENTS 4,160,818  7/1979  Smith et al. ..................... 424/12

(List continued on next page.)

FOREIGN PATENT DOCUMENTS 2111476  7/1983  Canada .
0226730  1/1987  European Pat. Off. .

OTHER PUBLICATIONS

A. Nagy, et al, "Quantitative Determination Of Imipramine And Desipramine In Human Blood Plasma By Direct Densitometry Of Thin–Layer Chromatograms", J. Pharmac., vol. 25, pp. 599–603 (1973).

R. Lucek, et al, "Specific Radioimmunoassay For Amitriptyline And Nortriptyline In Plasma", Research Communications in Chemical Pathology and Pharmacology, vol., 18(1), pp. 125–136 (Sep. 1977).

(List continued on next page.)

Primary Examiner—Mary E. Ceperley
Attorney, Agent, or Firm—Daniel W. Collins; Gregory W. Steele

[57] ABSTRACT

Immunoassay methods and reagents for the specific quantification of amitriptyline or nortriptyline in a test sample are disclosed employing antibodies prepared with amitriptyline or nortriptyline derivatives of the Formula III:

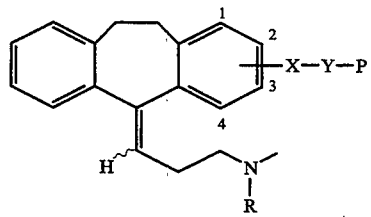

wherein for amitriptyline, R is $CH_3$, and for nortriptyline, R is H. The present invention also describes the synthesis of unique fluorescein tracers of the structure of Formula IV and Formula V:

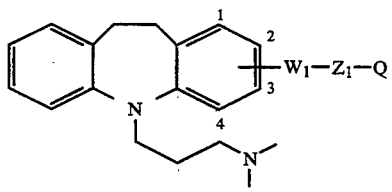

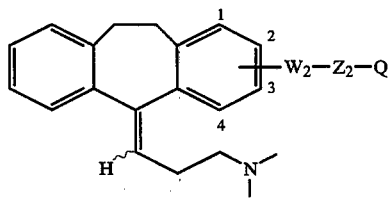

wherein for a specific amitriptyline immunoassay, $W_1$ is a heteroatom linked to the aromatic ring at the 2 or 3 position, and for a specific nortriptyline immunoassay, $W_2$ is two heteroatoms linked together and attached to the aromatic ring at the 2 or 3 position, and wherein Q is a detectable moiety, preferably fluorescein or a fluorescein derivative.

22 Claims, 25 Drawing Sheets

U.S. PATENT DOCUMENTS

| | | | |
|---|---|---|---|
| 4,223,013 | 9/1980 | Hu et al. | 425/85 |
| 4,275,160 | 6/1981 | Singh et al. | 435/188 |
| 4,307,245 | 12/1981 | Hu et al. | 562/442 |
| 4,420,568 | 12/1983 | Wang et al. | 436/536 |
| 4,495,281 | 1/1985 | Buckler et al. | 436/536 |
| 4,551,275 | 11/1985 | Pirio et al. | 435/188 |
| 4,585,862 | 4/1986 | Wang et al. | 544/319 |
| 4,629,691 | 12/1986 | Collins et al. | 435/4 |
| 4,668,640 | 5/1987 | Wang et al. | 436/536 |
| 4,795,822 | 1/1989 | Hu et al. | 560/10 |

OTHER PUBLICATIONS

M. N. Al-Bassam, et al, "Double-Antibody Enzyme Immunoassay For Nortriptyline", Clinical Chemistry, vol., 24(9), pp. 1590–1594 (1978).

G. P. Mould et al, "Radioimmunoassay Of Amitriptyline And Nortriptyline In Body Fluids", Annals of Clinical Biochemistry, vol., 15 pp. 221–225 (1978).

J. W. Hubbard, et al, "Radioimmunoassay For Psychotropic Drugs II: Synthesis And Properties Of Haptens For Tricyclic Antidepressants", Journal of Pharmaecentical Sciences, vol., 67 (11), pp. 1571–1578 (1978).

W. A. Garland, et al, "A Method For The Determination Of Amitriptyline And Its Metabolites Nortriptyline, 10-Hydroxyamitriptyline, And 10-Hydroxynortriptyline In Human Plasma Using Stable Isotope Dilution And Gas Chromatography-Chemical Ionization Mass Spectrometry (GC-CIMS)", Clin. Chamacol. Ther., vol. 25(6), pp. 844–856 (1979).

R. Virtanen, et al, "Radioimmunoassay For Tricyclic Antidepressants", Scand. J. clin. Lab. Invest., vol. 40, pp. 191–197 (1980).

J. F. Sayegh, "A Simplified Radioimmunoassay Of Plasma Nortriptyline In Depressed Patients Compared With High-Pressure Liquid Chromatography And Gas-Liquid Chromatography", Neurochemical Research, vol., 11(2), pp. 193–206 (1986).

S. Pankey, et al, "Quantitative Homogeneous Enzyme Immunoassays For Amitriptyline, Nortriptyline, Imipramine, And Desipramine", Clin. Chem., vol. 32(5), pp. 768–772 (1986).

H. Denis, et al, "Enzyme-Linked Immunosorbent Assay For Amitriptyline And Other Antidepressants Using A Monoclonal Antibody", Clinica Chimica Acta, vol., 159 pp. 257–267 (1986).

M. Bowles, et al, "Large Scale Production And Purification Of Paraquat And Desipramine Monoclonal Antibodies And Their Fab Fragments", Int. J. Immunopharmac., vol. 10,(5), pp. 537–545 (1988).

R. Cameron Dorey, et al, "Results Compared For Tricyclic Antidepressants As Assayed By Liquid Chromatography And Enzyme Immunoassay", Clin, Chem., vol. 34(11), pp. 2348–2351 (1988).

I. Lavastre, et al, "The Synthesis Of Metallocene-Labelled Drugs For Biological Assays", Applied Organometallic Chemistry, vol. 4, pp. 9–17 (1990).

D. J. Windzor, et al, "Adaptation Of The Muller Method To Allow Quantitative Characterization Of The Affinity And Cross-Reactivity Of Antibodies By Competitive Radioimmunoassay", Molecular Immunology, vol. 28 (9), pp. 995–1001 (1991).

Syva, "Practical Considerations For The Evaluation Of The Emit ® Tricyclic Antidepressant Assays", Emit ® Quantitative Tricyclic Antidepressant Assays, pp. 1–13 (1986).

P. K. Sonsalla, et al, "An Evaluation Of The Emit ®st Assay For The Detection Of Tricyclic Antidepressant Drugs In Plasma Or Serum", Clinical Toxicology, vol., 22(1), pp. 63–76 (1984).

K. K. Midha, et al, "Monitoring Of Therapeutic Concentrations Of Psychotropic Drugs In Plasma By Radioimmunoassays", Journal of Analytic Toxicology, vol., 2, pp. 185–192 (Sep./Oct. 1978).

| COMPOUND | TRACER (30) (% CROSSREACTIVITY) | TRACER (27) (% CROSSREACTIVITY) |
| --- | --- | --- |
| NORTRIPTYLINE | 39 | 6 |
| (Z)-10-OH AMITRIPTYLINE | 50 | 12 |
| (E)-10-OH AMITRIPTYLINE | 53 | 13 |
| (Z)-10-OH NORTRIPTYLINE | 7 | 1 |
| (E)-10-OH NORTRIPTYLINE | 11 | 1 |

(Z)-10-OH AMITRIPTYLINE     (E)-10-OH AMITRIPTYLINE (Z)-10-OH NORTRIPTYLINE     (E)-10-OH NORTRIPTYLINE

| COMPOUND | TRACER (31) (% CROSSREACTIVITY) | TRACER (29) (% CROSSREACTIVITY) |
|---|---|---|
| AMITRIPTYLINE | 14 | 3 |
| (E)-10-OH AMITRIPTYLINE | 2 | 3 |
| (E)-10-OH NORTRIPTYLINE | 21 | 7 |

(Z)-10-OH AMITRIPTYLINE (E)-10-OH AMITRIPTYLINE (Z)-10-OH NORTRIPTYLINE (E)-10-OH NORTRIPTYLINE

REAGENTS AND METHODS FOR THE QUANTIFICATION OF AMITRIPTYLINE OR NORTRIPTYLINE IN BIOLOGICAL FLUIDS

This application is a continuation-in-part application of U.S. patent application Ser. No. 07/738,635, filed July 31, 1991, abandoned.

FIELD OF THE INVENTION

The present invention relates to the immunoassay quantification of amitriptyline in a test sample or nortriptyline in a test sample. In particular, the present invention relates to immunogens, antibodies prepared from such immunogens, and labeled reagents for the specific quantification of amitriptyline in the presence of its metabolites, and for the specific quantification of nortriptyline in the presence of its metabolites and amitriptyline, preferably for use in a fluorescence polarization immunoassays.

BACKGROUND OF THE INVENTION

Amitriptyline and nortriptyline are tricyclic antidepressant drugs which are prescribed for the treatment of chronic depression and are represented by Formula I and Formula II, respectively:

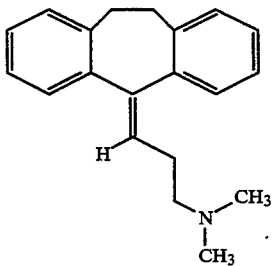

I

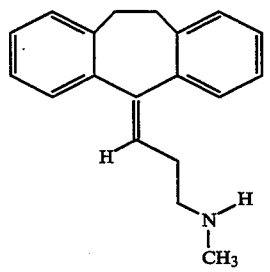

II

When amitriptyline is the primary drug for such treatment, nortriptyline is usually present as a naturally occurring metabolite produced by demethylation of the tertiary nitrogen of amitriptyline. Accordingly, nortriptyline is not only present when it is prescribed as the primary drug for treatment of chronic depression, but is also present when amitriptyline is employed as the primary drug for such treatment.

The monitoring of therapeutic drug levels of amitriptyline and nortriptyline in biological fluids such as serum, plasma, whole blood, urine, and the like, has become very useful to provide physicians with information to aid in patient management. The monitoring of such drug levels enables adjustment of patient dosage to achieve optimal therapeutic effects, and helps avoid either subtherapeutic or toxic levels, especially in the case of treatment with amitriptyline which results in the presence of both amitriptyline and nortriptyline. In this regard, since high levels of amitriptyline and nortriptyline have been associated with central nervous system disorders, cardiovascular toxicity, hypertension, seizures, coma and death, the concentration of amitriptyline and nortriptyline in a patient's blood must be maintained in a therapeutic range, particularly since a wide interpatient variation normally exists in human plasma for a given dose.

Accordingly, since individuals vary greatly in their response to treatment with amitriptyline or nortriptyline, it is necessary to monitor the therapy by measuring both the levels of amitriptyline and nortriptyline where amitriptyline is the primary drug for treatment, or measuring the level of nortriptyline where nortriptyline is the primary drug for treatment, in, for example, the serum or plasma of the patient. Concentrations below the desired therapeutic ranges are proposed to be subtherapeutic for the treatment of depression, while levels higher than the range can be associated with undesirable effects including cardiovascular complications, anticholinergic effects, and sedation, without any increase in antidepressant efficacy.

The measurement of amitriptyline and nortriptyline levels by chromatographic techniques, such as high pressure liquid chromato-graphy [Dorey, et al., Clin. Chem., 34, 2348-2351 (1988)], gas chromatography [Garland, et al., Clin. Pharmacol. Ther., 25, 844-856 (1979)], thin-layer chromatography [Nagy, et al., J. Pharm. Pharmacol., 25, 599-603 (1973)], have been described. However, such techniques are labor intensive, requiring highly skilled personnel to perform various cumbersome steps which are time consuming and tedious.

The immunoassay determination of the levels of tricyclic antidepressant drugs, such as by radioimmunoassay (RIA) techniques [Sayegh, Neurochem. Res., 11, 193-206 (1986); Virtanen, Scand. J. Clin. Lab. Invest., 40, 191-197, (1980)], by enzyme linked immunosorbent assay (ELISA) techniques [Denis, et al., Clin. Chem. Acta, 159, 257-267 (1986)], by fluorescence polarization immunoassay (FPIA) techniques [U.S. Pat. No. 4,420,568 and European Patent Application No. 226,730], and by enzyme immunoassay (EIA) techniques [U.S. Pat. No. 4,307,245, U.S. Pat. No. 4,223,013 and Pankey et. al., Clin. Chem., 32, 768-772 (1986)], have been described. However, these techniques suffer from either a lack of specificity, i.e. determination of amitriptyline in the presence of nortriptyline and amitriptyline metabolites and determination of nortriptyline in the presence of amitriptyline and nortriptyline metabolites, or require labor-intensive column purification to overcome the lack of antibody specificity in the presence of the analyte's metabolites. In particular, a nonspecific fluorescence polarization immunoassay (FPIA) for the detection of the total amount of the four major tricyclic antidepressant drugs is commercially available and described in European Patent Application Publication No. 226,730 and U.S. Pat. No. 4,420,568 wherein the concentration determined by this assay is only an estimation of the total amount of tricyclic antidepressant in plasma or serum. Accordingly, such assay cannot be used to accurately quantify a specific individual tricyclic antidepressant drug, for example, in a patient treated with amitriptyline, but instead, would give the total amount of amitriptyline and nortriptyline in the patient's plasma or serum.

SUMMARY OF THE INVENTION

The present invention provides unique antibody reagents and labeled reagents for the quantification of amitriptyline or nortriptyline in a test sample. The present invention also provides synthetic procedures for preparing immunogens which are employed for the production of such antibody reagents, and for preparing such labeled reagents. According to the present invention, the labeled reagents and the antibody reagents offer an advance in the art beyond previously known procedures when used in an immunoassay for the quantification of amitriptyline or nortriptyline in a test sample. According to a preferred embodiment of the present invention, labeled reagents and antibody reagents are described for use in a fluorescence polarization immunoassay which combines the specificity of an immunoassay with the speed and convenience of homogeneous methods to provide the precise and reliable quantification of amitriptyline or nortriptyline in a test sample.

DETAILED DESCRIPTION OF THE INVENTION

According to the present invention, the specific quantification of amitriptyline or nortriptyline is accomplished by first contacting the test sample with a labeled reagent or tracer and an antibody reagent, either simultaneously or sequentially in either order, and then measuring the amount of the labeled reagent which either has or has not participated in a binding reaction with the antibody reagent as a function of the amount of amitriptyline or nortriptyline in the test sample. In particular, the present invention relates to immunogens, antibodies prepared from such immunogens, and labeled reagents for use in the fluorescence polarization immunoassays for the specific quantification of amitriptyline and for use in the specific quantification of nortriptyline. It is to be understood that the specific quantification of amitriptyline or nortriptyline according to the present invention is intended to mean that, for an amitriptyline immunoassay, the specific quantification of amitriptyline is accomplished in the presence of nortriptyline and amitriptyline metabolites, and for a nortriptyline immunoassay, the specific quantification of nortriptyline is accomplished in the presence of amitriptyline and nortriptyline metabolites.

Antibodies of the present invention are produced with immunogens which are prepared with derivatives of the Formula III:

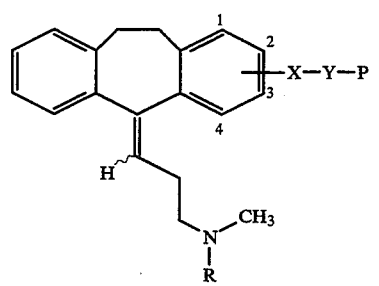

wherein P is an immunogenic carrier material and the configuration is either E or Z or a combination of E and Z, and wherein for the quantification of amitriptyline, R is $CH_3$, X is two heteroatoms linked together and connected to the aromatic ring at either the 2 or 3 position, and Y is a linking group comprising from 0 to 6 carbon atoms, and for the quantification of nortriptyline, R is H, X is two heteroatoms linked together and connected to the aromatic ring at either the 2 or 3 position, and Y is a linking group comprising from 0 to 6 carbon atoms.

Labeled reagents of the present invention for amitriptyline are prepared with derivatives of the Formula IV:

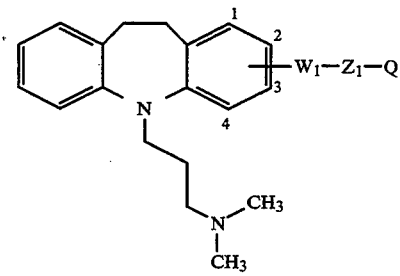

IV wherein Q is a detectable moiety, preferably a fluorescent moiety, and wherein for the quantification of amitriptyline, $W_1$ is a heteroatom connected to the aromatic ring at either the 2 or 3 position, $Z_1$ is a linking group comprising from 1 to 4 carbon atoms and 0 to 2 heteroatoms.

Labeled reagents of the present invention for nortriptyline are prepared with derivatives of the Formula V:

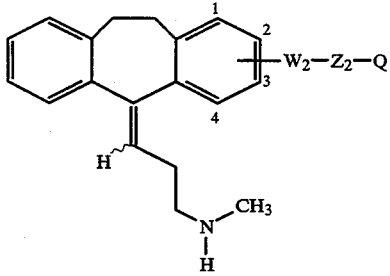

V wherein Q is a detectable moiety, preferably a fluorescent moiety, and the configuration is either E or Z or a combination of E and Z, and wherein for the quantification of nortriptyline, $W_2$ is two heteroatoms linked together and connected to the aromatic ring at either the 2 or 3 position, $Z_2$ is a linking group comprising from 1 to 4 carbon atoms and 0 to 2 heteroatoms.

Figure 1A:
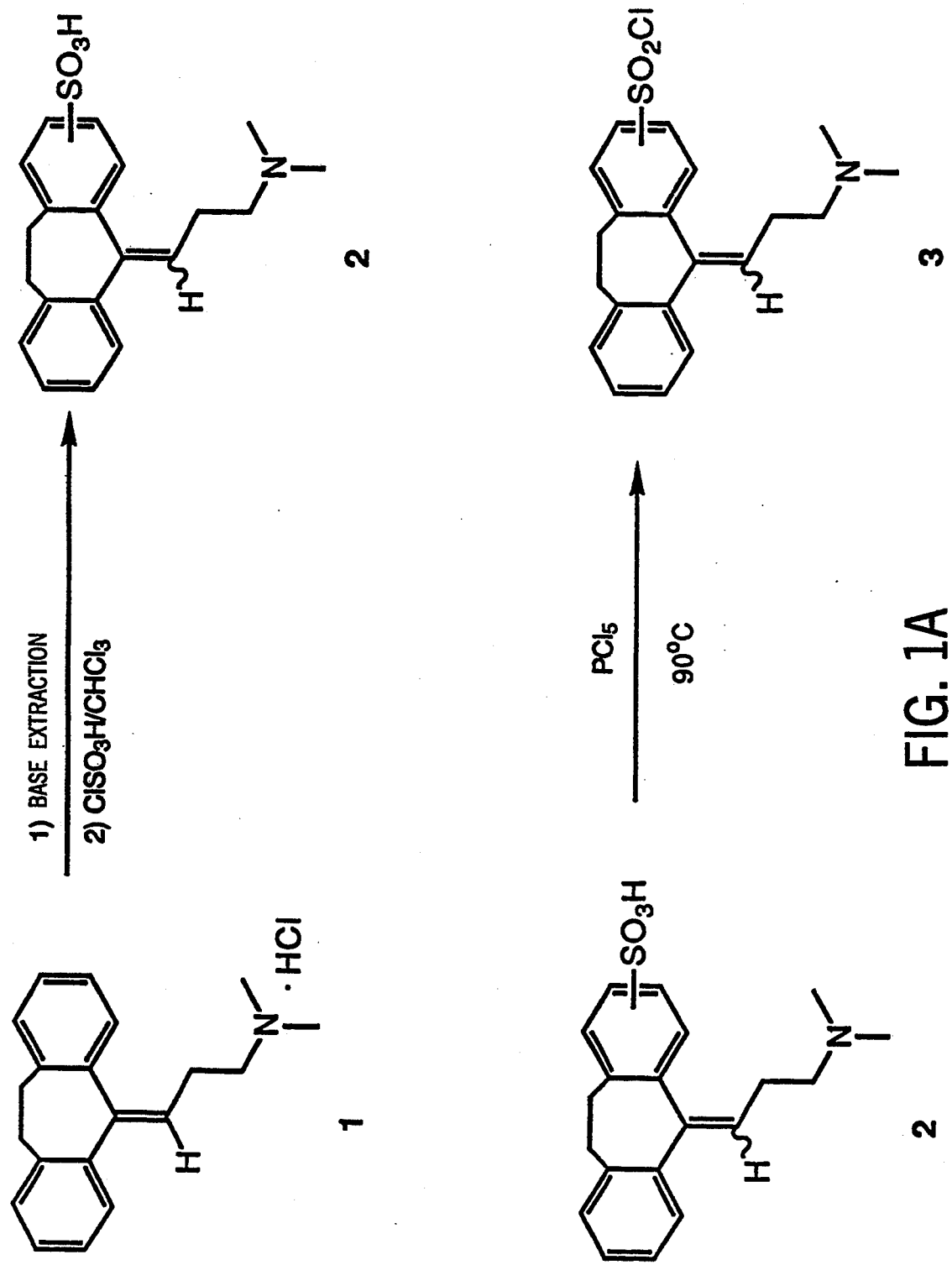
FIGS. 1A and 1B illustrate the synthetic pathway for coupling amitriptyline to bovine serum albumin according to the method of the present invention.
Figure 1B:
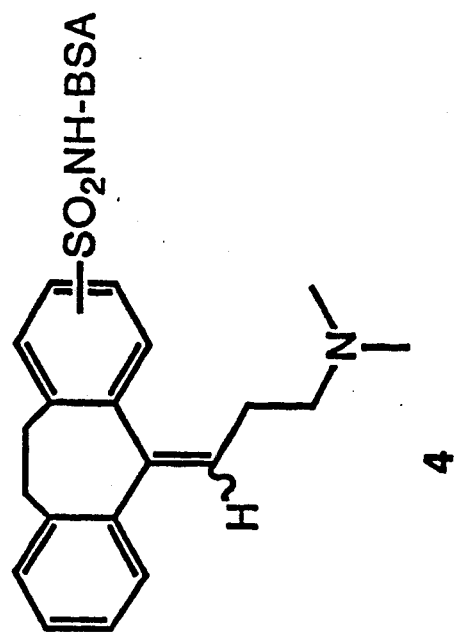
Figure 1B:
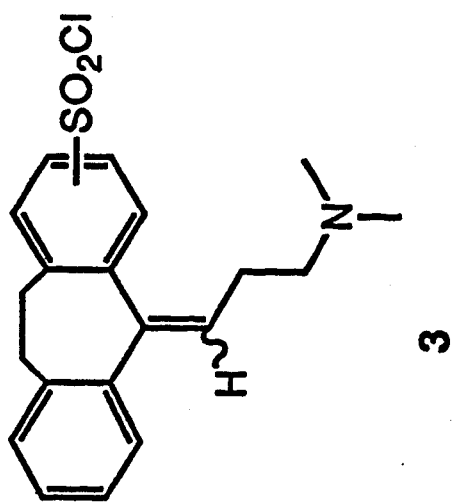
Figure 2A:
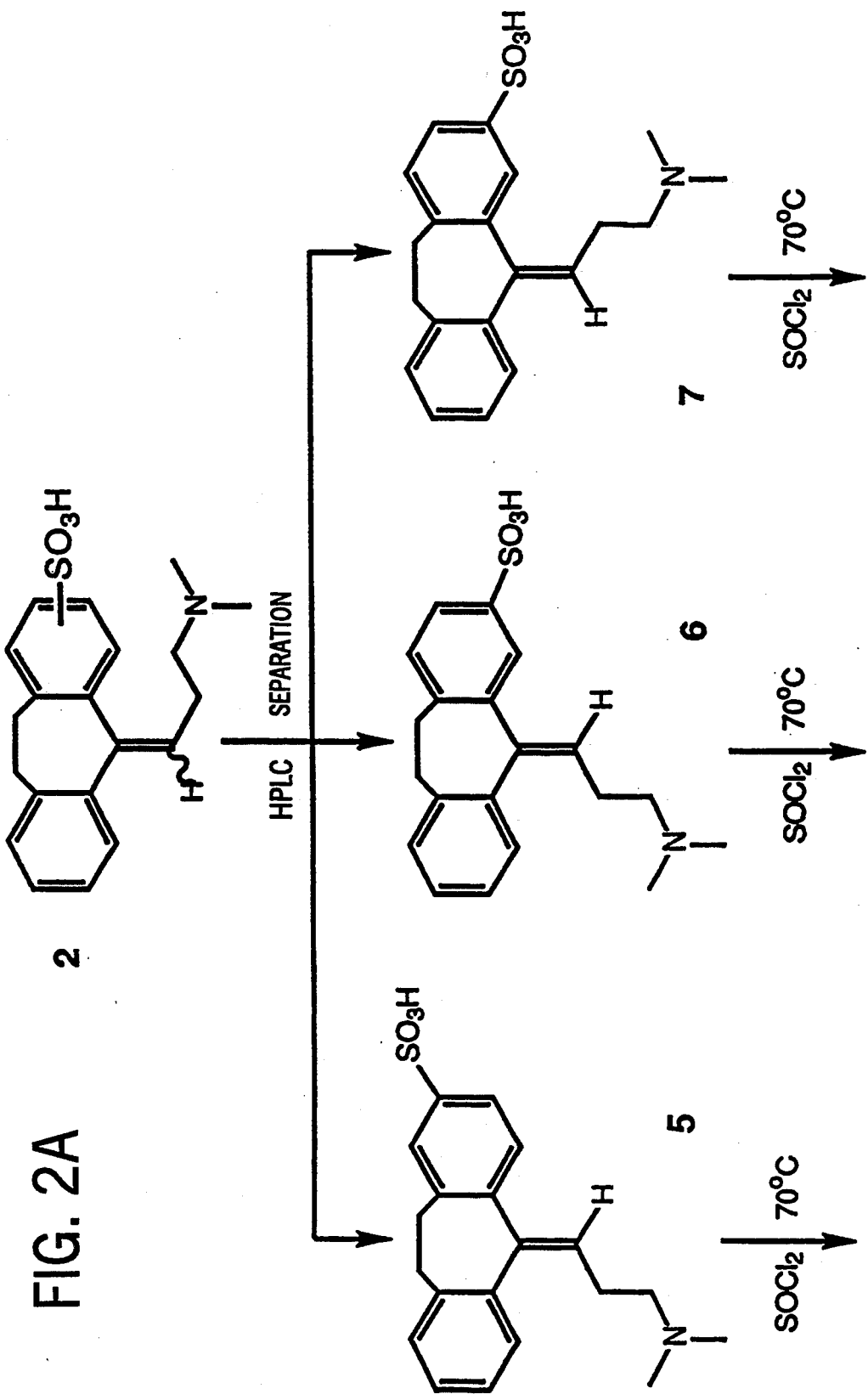
FIGS. 2A and 2B illustrate the synthetic pathway for coupling amitriptyline to bovine serum albumin according to the method of the present invention.
Figure 2B:
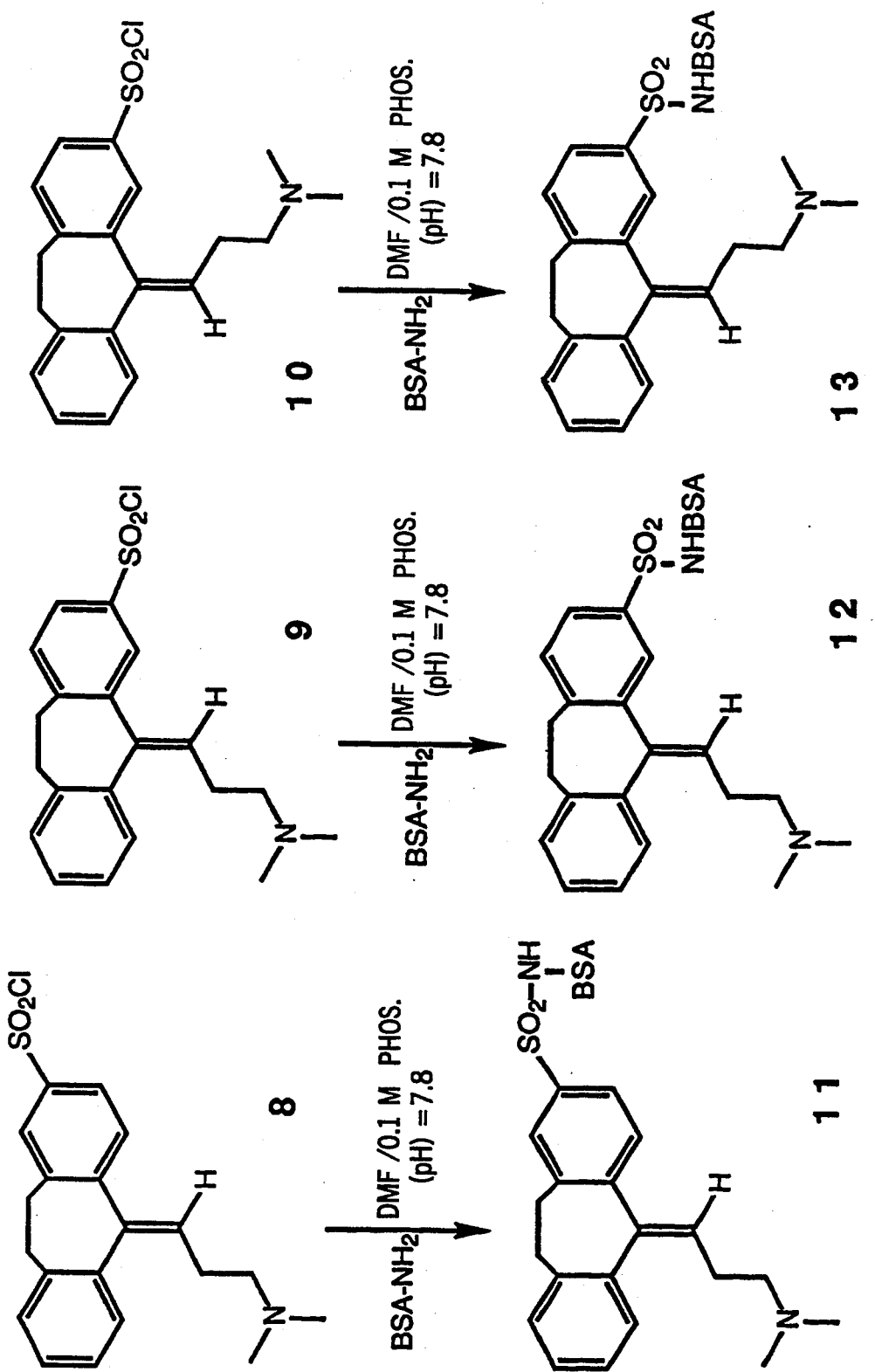
Figure 3A:
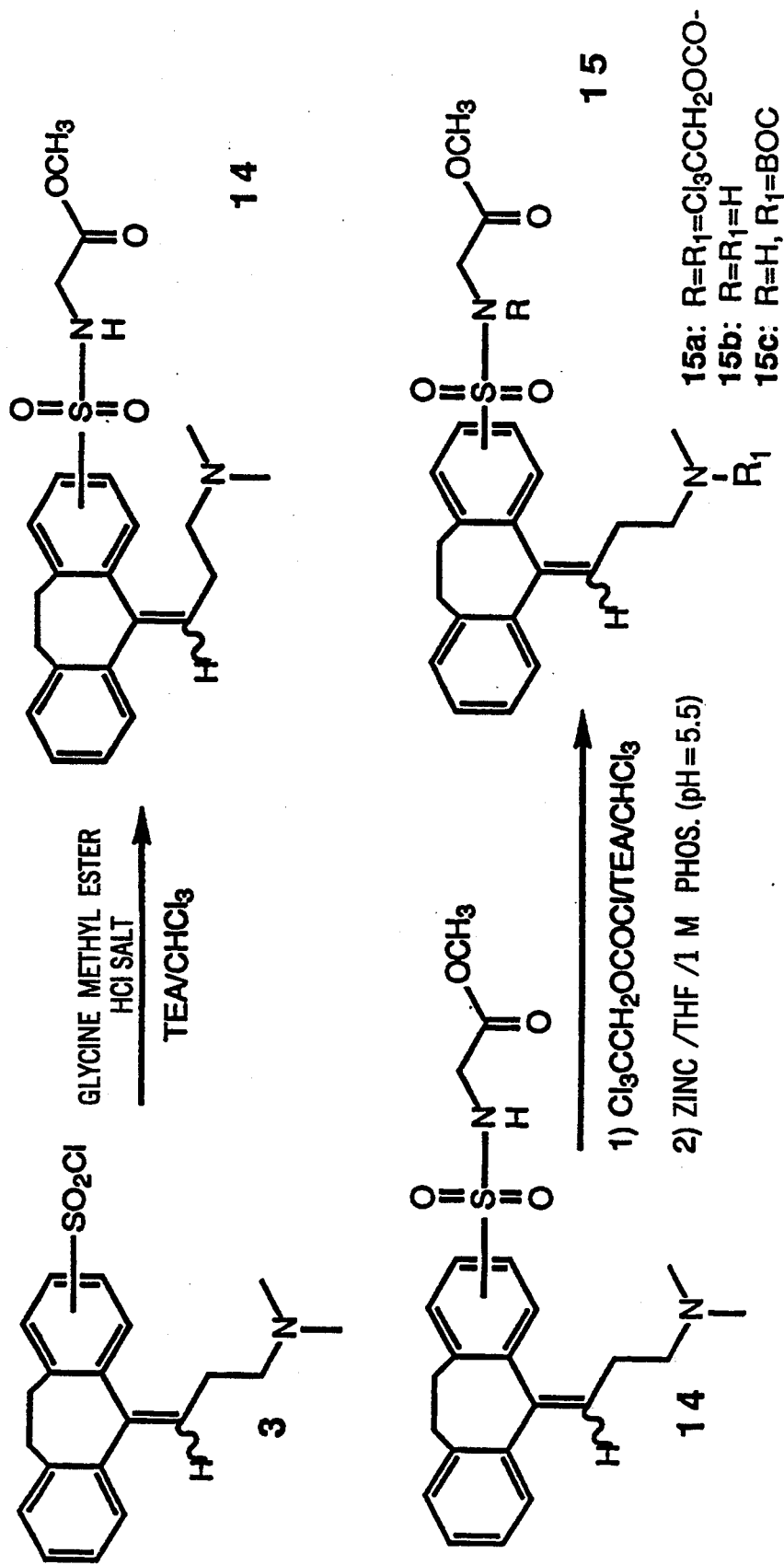
FIGS. 3A, 3B, and 3C illustrate the synthetic pathway for coupling nortriptyline to bovine serum albumin according to the method of the present invention.
Figure 3B:
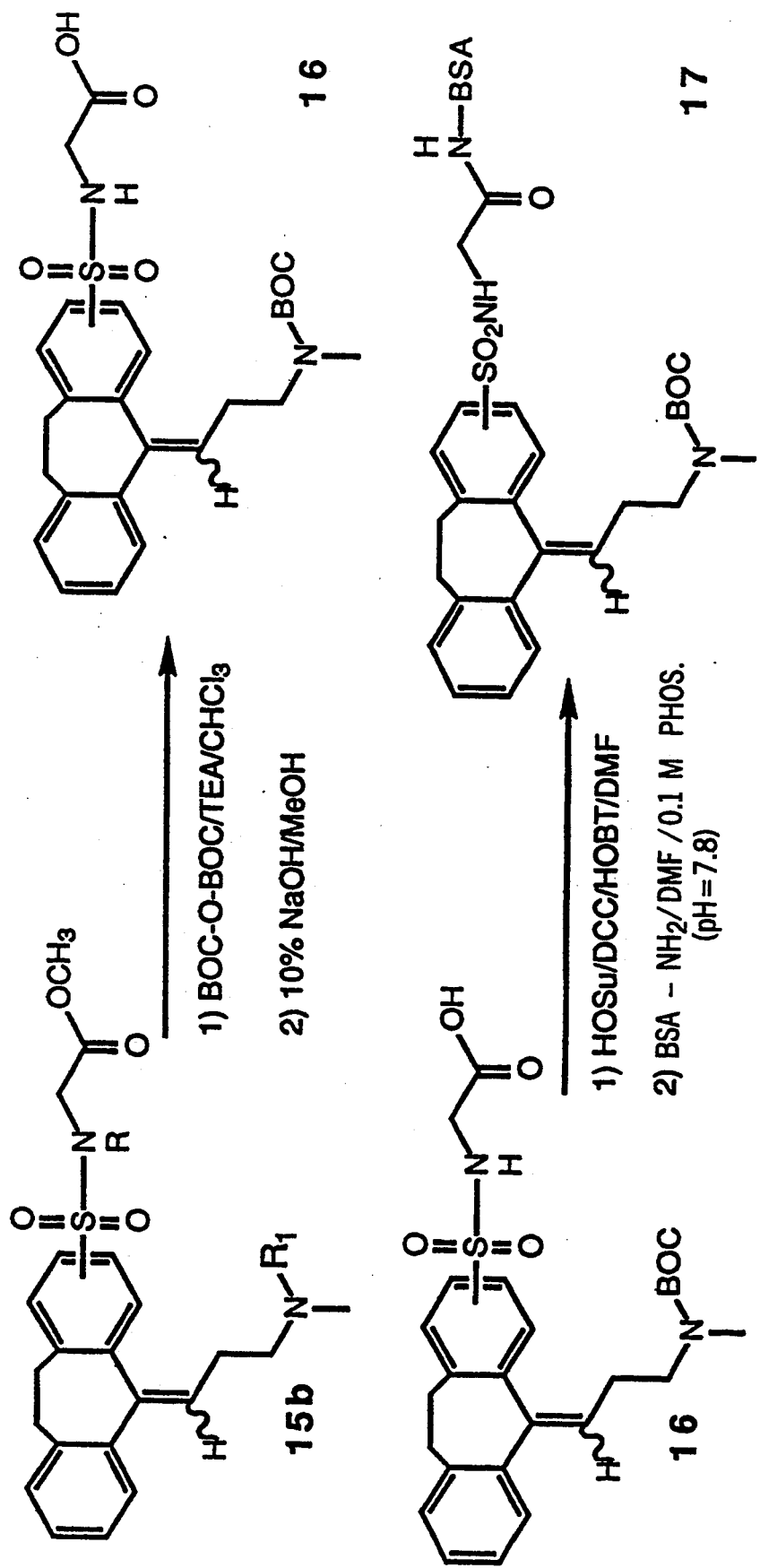
Figure 3C:
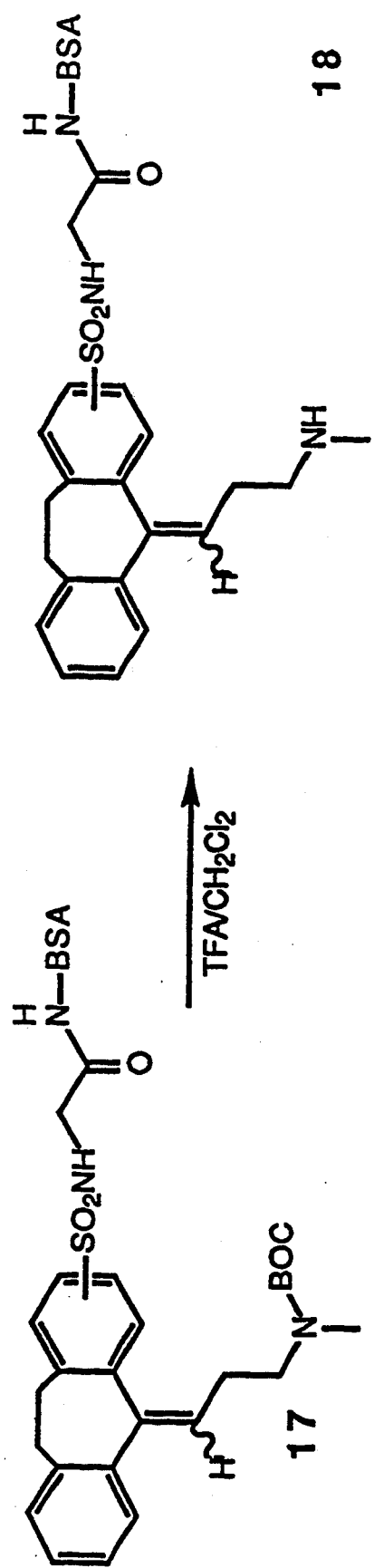
Figure 4A:
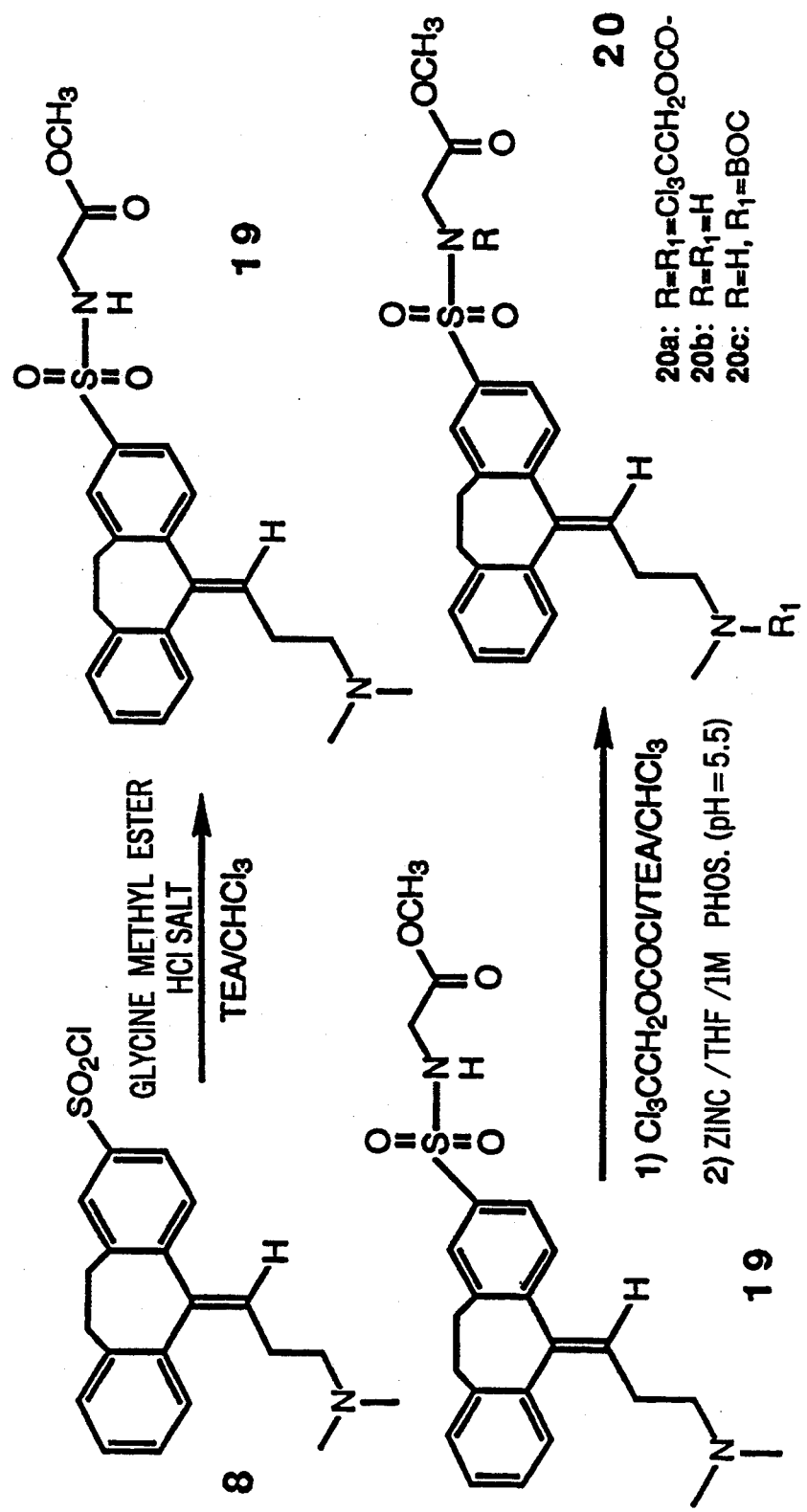
FIGS. 4A, 4B, and 4C illustrate the synthetic pathway for coupling nortriptyline to bovine serum albumin according to the method of the present invention.
Figure 4B:
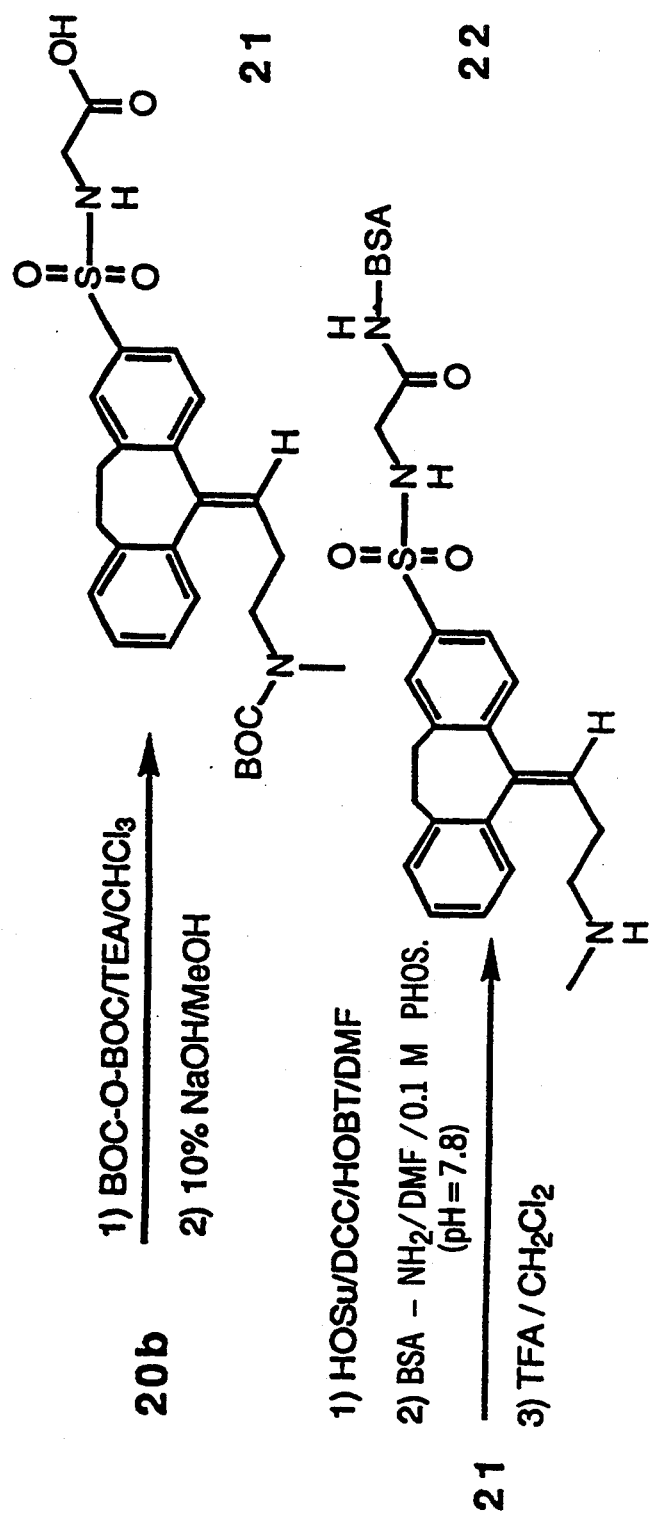
Figure 4C:
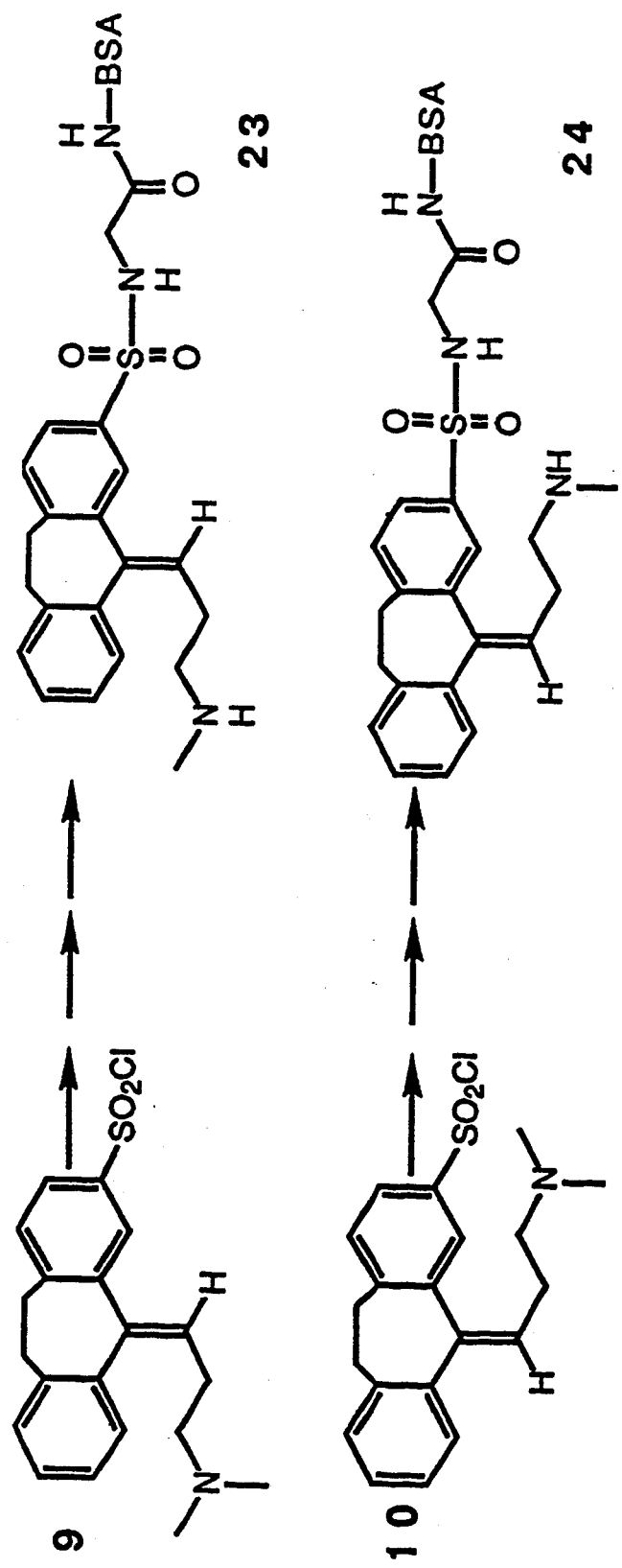
Figure 5A:
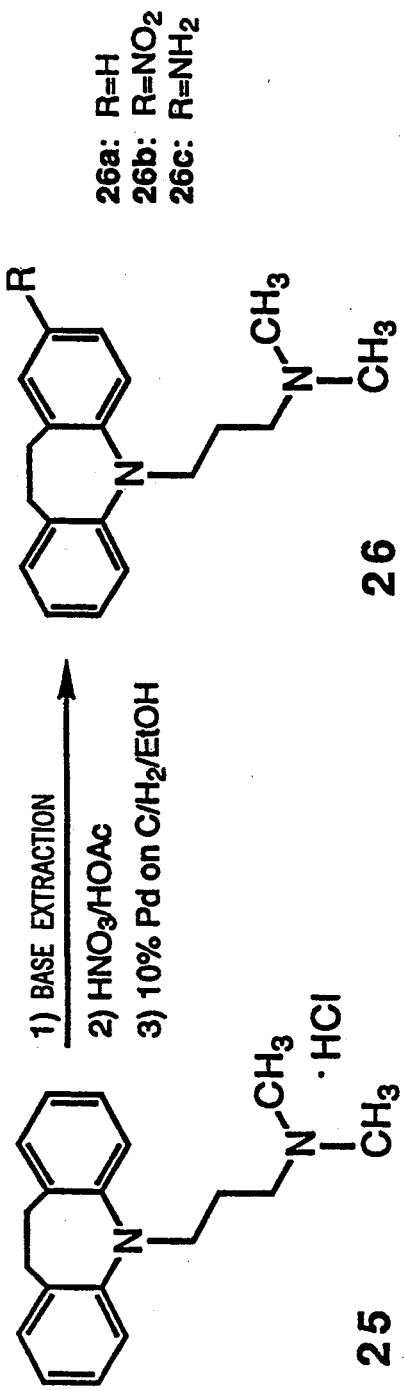
FIGS. 5A and 5B illustrate the synthetic pathway for the preparation of a fluorescent tracer for an amitriptyline assay according to the method of the present invention.
Figure 5A:
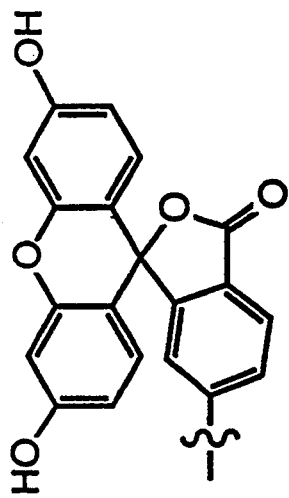
Figure 5A:
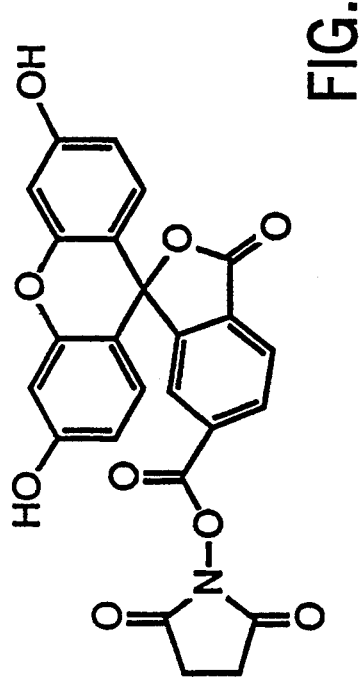
Figure 5B:
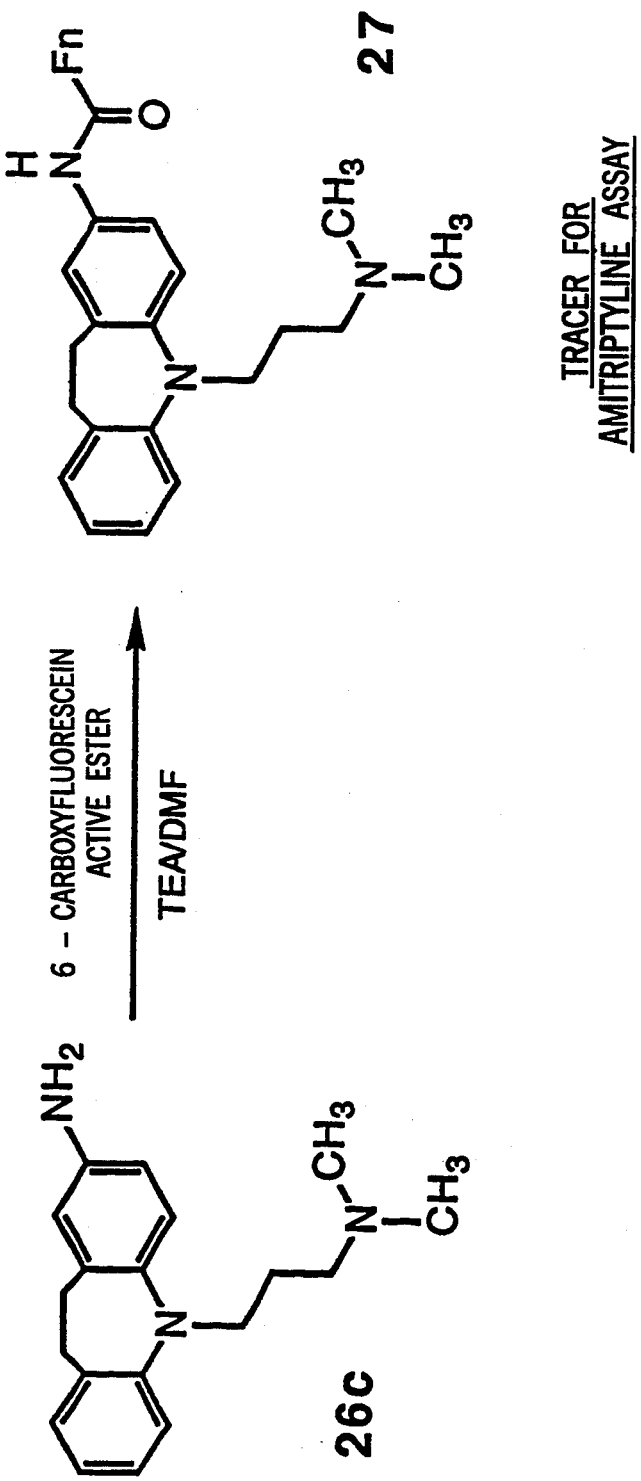
Figure 6A:
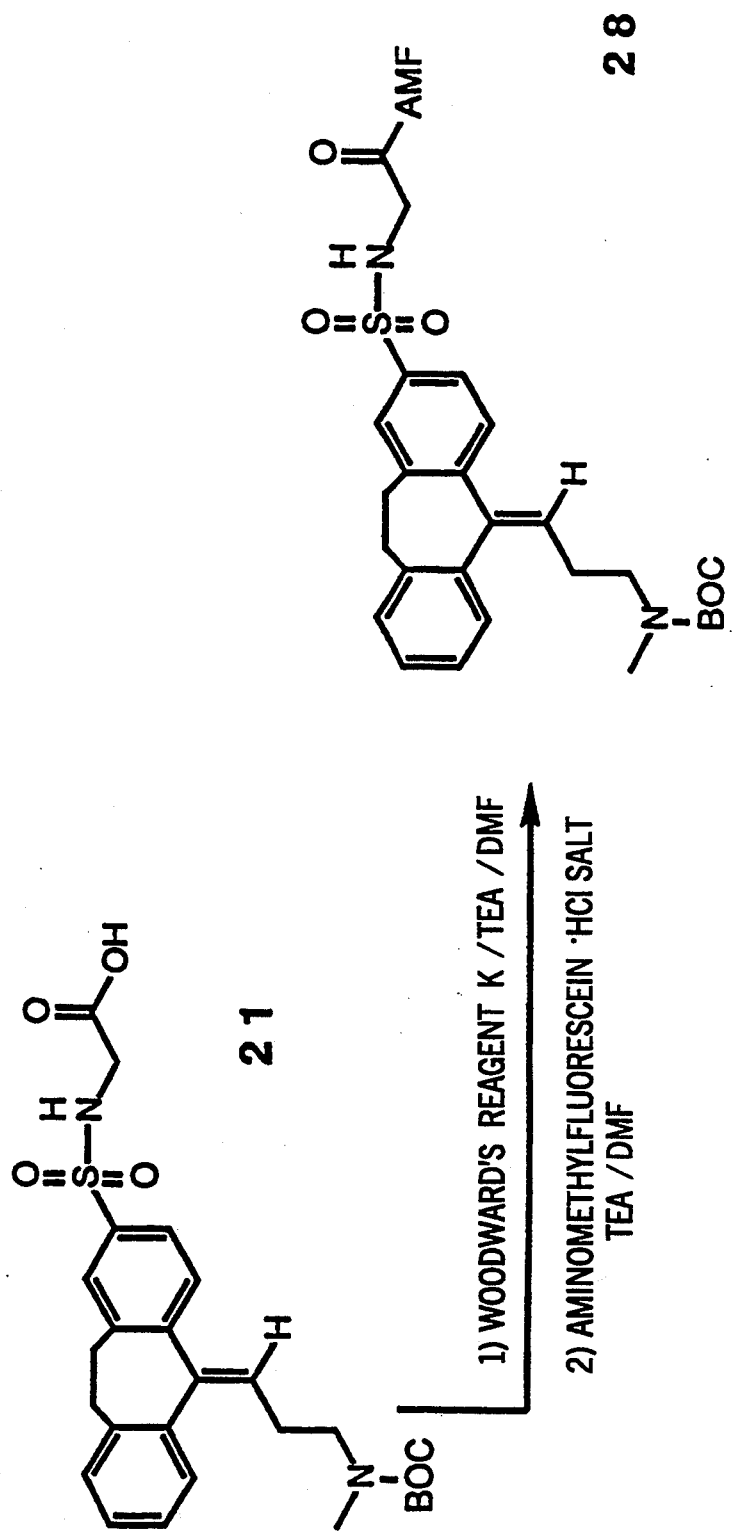
FIGS. 6A, 6B and 6C illustrate the synthetic pathway for the preparation of a fluorescent tracer for a nortriptyline assay according to the method of the present invention.
Figure 6B:
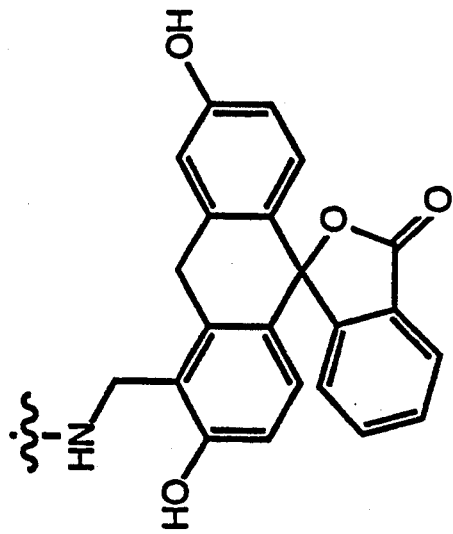
Figure 6B:
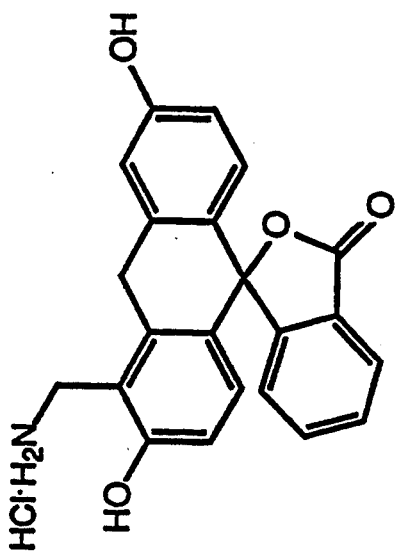
Figure 6C:
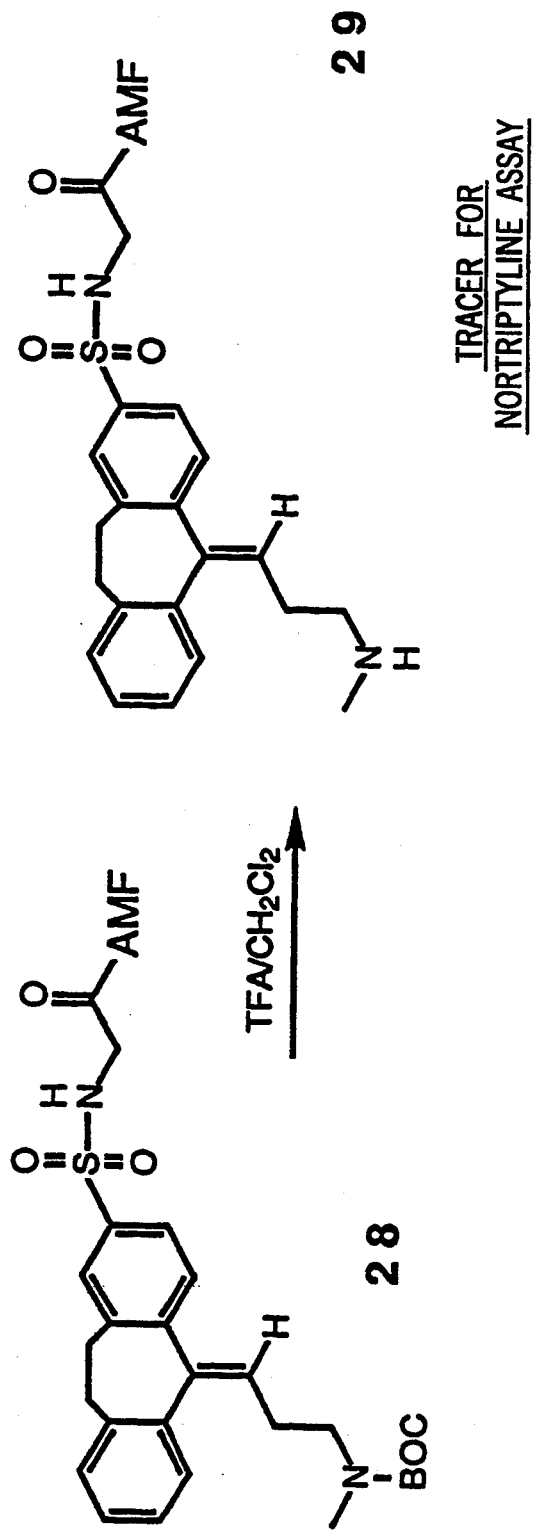

The immunogens described above were prepared as described below and as shown in FIGS. 1 and 2 (amitriptyline immunogens) and as shown in FIGS. 3 and 4 (nortriptyline immunogens). For amitriptyline, a mixture of E and Z, 2-substituted or 3-substituted amitriptyline sulfonic acids resulted from the treatment of the amitripyline free base with chlorosulfonic acid. The resulting mixture was then converted to the sulfonyl chloride which was reacted with bovine serum albumin to give the desired amitriptyline immunogen (FIG. 1). Additionally, the mixture of sulfonic acids was separated by HPLC to give pure 2E-amitriptyline sulfonic acid as well as the 2Z and 3E isomers. Each of these isomers was converted into an amitriptyline immunogen by the method used for the mixture of amitriptyline sulfonic acids described above (FIG. 2). For the preparation of nortriptyline immunogens, the synthetic sequence began with a mixture of amitriptyline sulfonyl chlorides which was reacted with glycine methyl ester to give a methyl ester sulfonamide. The mixture of sulfonamides was converted to the N'-BOC protected carboxylic acid via an N'-demethylation, hydrolysis sequence followed by N'-BOC protection. This mixture of acids was coupled to bovine serum albumin via an hydroxysuccinimido active ester, the resulting intermediate was treated with trifluoroacetic acid to give the desired nortriptyline immunogen (FIG. 3). Additionally, the mixture of amitriptyline sulfonic acids was separated by HPLC to give pure 2E-amitriptyline sulfonic acid, as well as the 2Z and 3E isomers, which were converted to the respective sulfonyl chlorides and ultimately to the desired nortriptyline immunogens as shown in FIG. 4.

A preferred fluorescent labeled reagent as described above for use in a specific fluorescence polarization immunoassay for amitriptyline was synthesized by condensing 2-aminoimipramine with the 6-carboxyfluorescein hydroxysuccinimido active ester to afford the amitriptyline tracer as shown in FIG. 5. A preferred fluorescent nortriptyline labeled reagent as described above for use in a specific fluorescence polarization immunoassay for nortriptyline was synthesized by treating 2E-chlorosulfonyl amitriptyline with glycine methyl ester to yield a sulfonamide which was demethylated, hydrolyzed and protected as an N'-BOC derivative. The N'-BOC protected-2E-sulfonamide acid was condensed with the aminomethylfluorescein to afford the N'-BOC protected tracer. After treatment with trifluoroacetic acid, the desired nortriptyline tracer shown in FIG. 6 was obtained.

When following a fluorescence polarization immunoassay (FPIA) format employing the reagents according to the present invention, the concentration, or level, of either amitriptyline or nortriptyline in a test sample can be accurately quantified. To perform a FPIA for the specific quantification of amitriptyline or nortriptyline, calibration curves were generated for monitoring the therapeutic range of amitriptyline (FIG. 7) and nortriptyline (FIG. 8).

According to the present invention, it has been unexpectedly and surprisingly found that superior fluorescence polarization immunoassay assay results for the quantification of amitriptyline or nortriptyline are obtained when employing (i) an antibody reagent comprising antibodies produced from an amitriptyline or nortriptyline immunogen of Formula III where P is an immunogenic carrier as described above and (ii) a fluorescent labeled reagent of Formula IV (amitriptyline) or Formula V (nortriptyline) where Q is a fluorescent moiety as described above. For the quantification of amitriptyline, the antibody reagent comprises antibodies which are capable of binding to or recognizing amitriptyline wherein the antibodies are preferably produced with an immunogen prepared from the amitriptyline derivative of Formula III where P is bovine serum albumin, X is —$SO_2$—NH—, R is $CH_3$, and Y is 0 carbon atoms, and the labeled reagent is preferably prepared from the derivative of Formula IV where Q is a fluorescent moiety, $W_1$ is —NH—, and $Z_1$ is —CO—. Similarly, for the quantification of nortriptyline, the antibody reagent comprises antibodies which are capable of binding to or recognizing nortriptyline wherein the antibodies are preferably produced with an immunogen prepared from the nortriptyline derivative of Formula III where P is bovine serum albumin, X is —$SO_2$—NH—, R is H, and Y is —$CH_2$—CO—, and the labeled reagent is preferably prepared from the nortriptyline derivative of Formula V where Q is a fluorescent moiety, $W_2$ is —NH—$SO_2$— and $Z_2$ is —$CH_2$—CO—.

Figure 9:
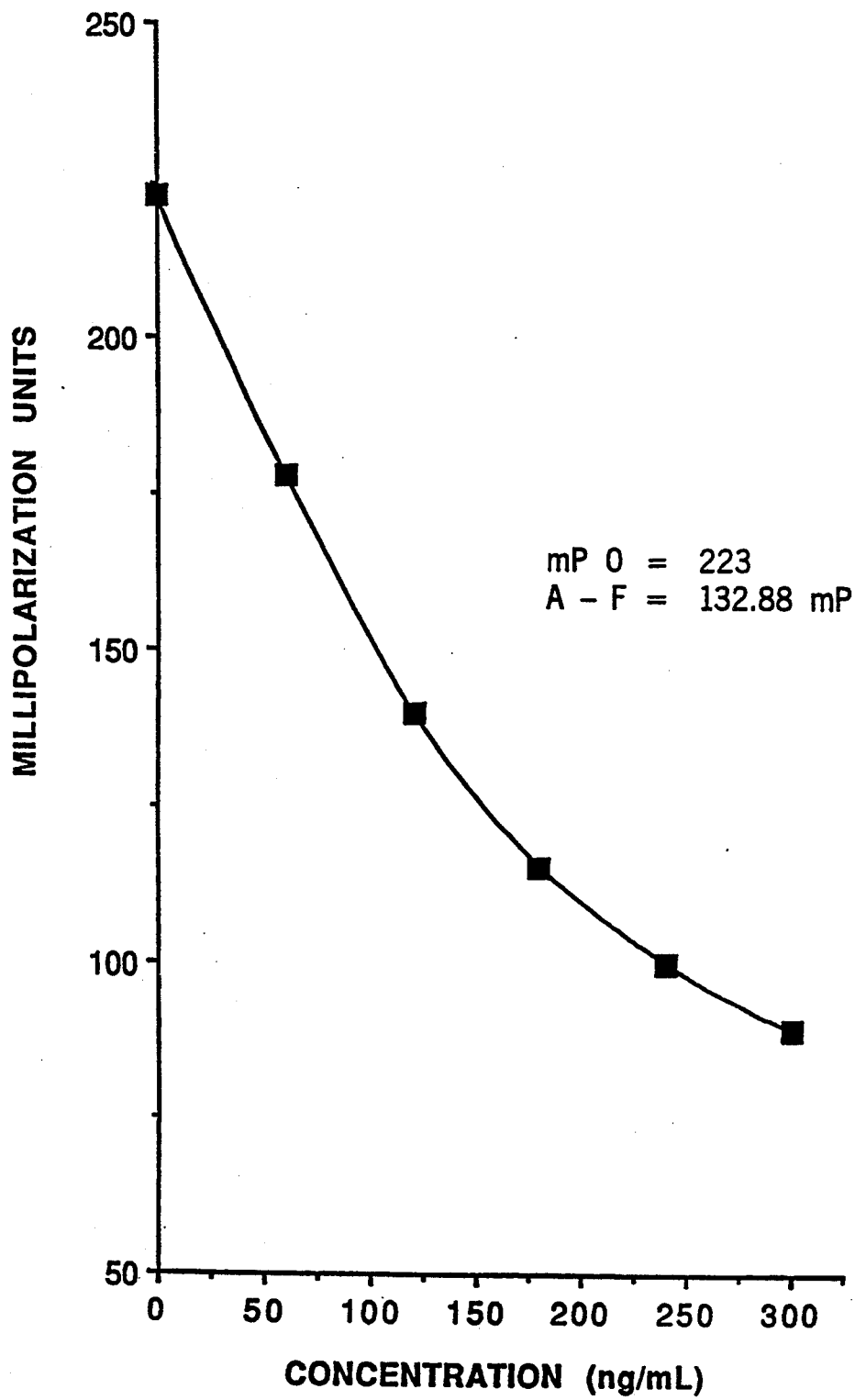
FIG. 9 is a graph which illustrates a nortriptyline calibration curve on the Abbott TDx ® analyzer.
Figure 10:
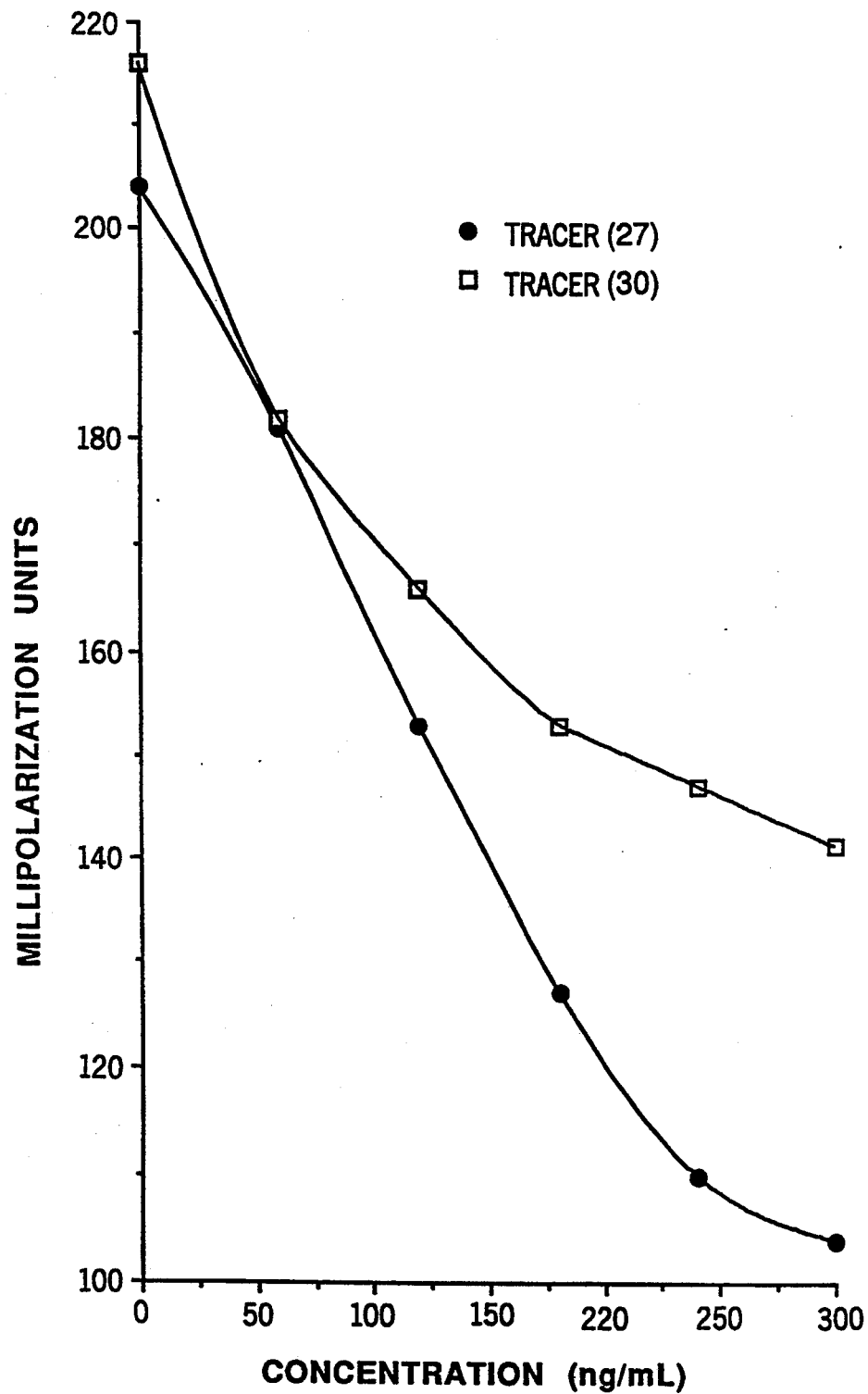
FIG. 10 is a graph which illustrates the effects of structural modification of the fluorescent tracer on a specific amitriptyline assay.
Figure 11:
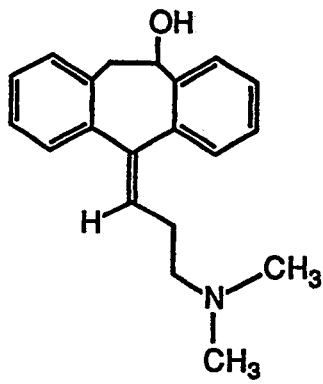
FIG. 11 is a table which illustrates the effects of structural modification of the fluorescent tracer on crossreactivity in a specific amitriptyline assay.
Figure 11:
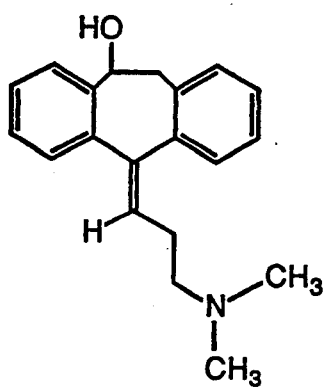
Figure 11:
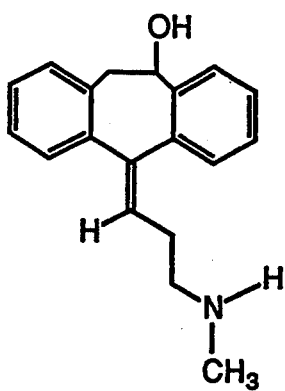
Figure 11:
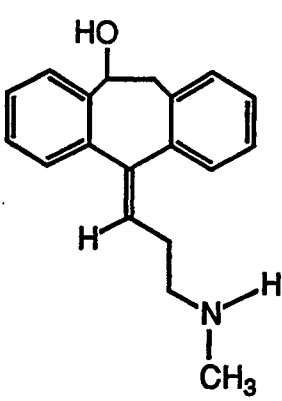
Figure 12:
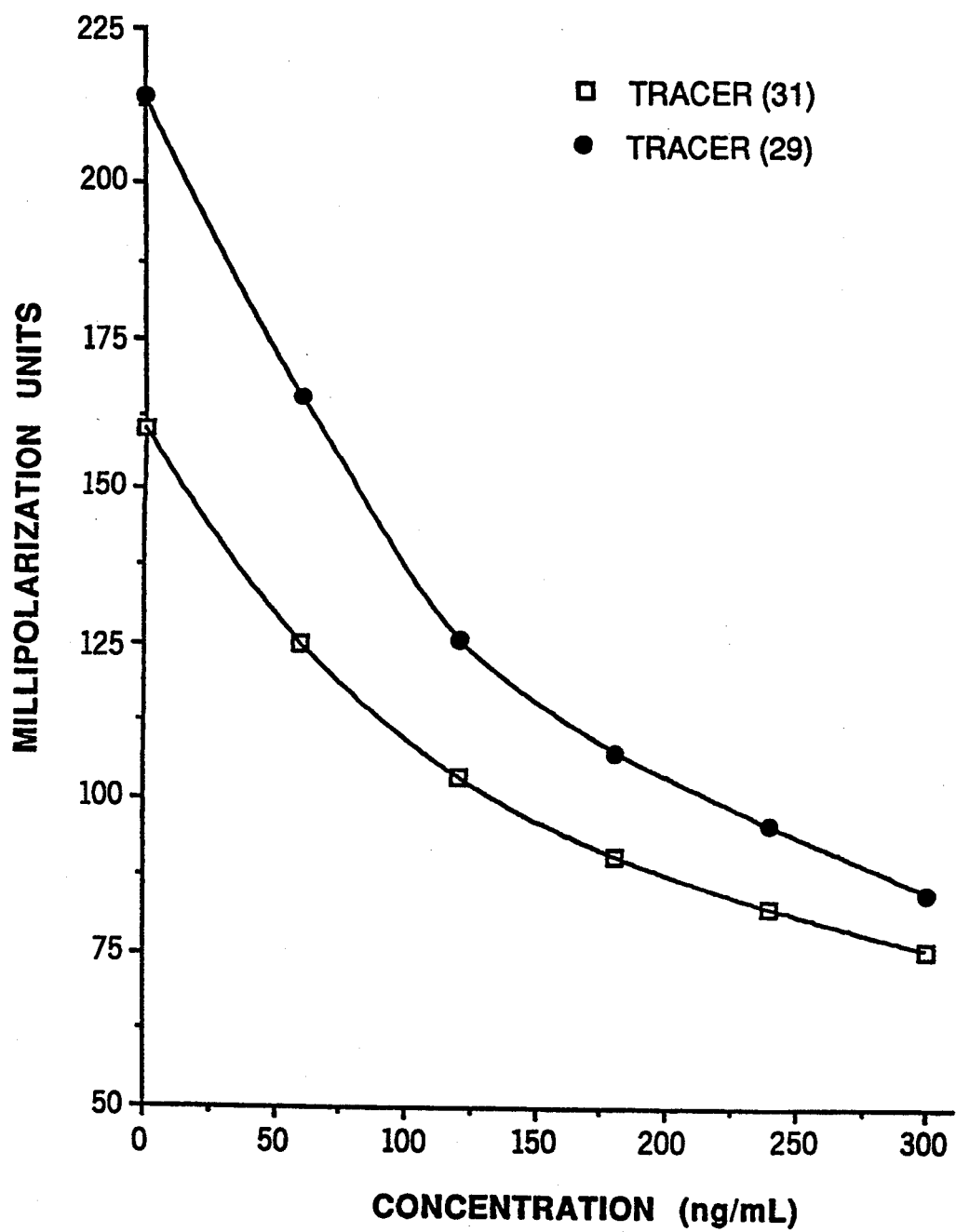
FIG. 12 is a graph which illustrates the effects of structural modification of the fluorescent tracer on a specific nortriptyline assay.
Figure 13:
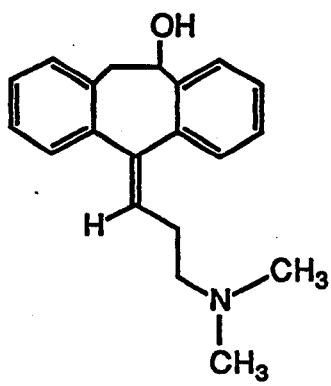
FIG. 13 is a table which illustrates the effects of structural modification of the fluorescent tracer on crossreactivity in a specific nortriptyline assay.
Figure 13:
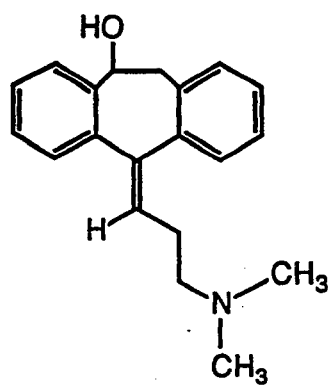
Figure 13:
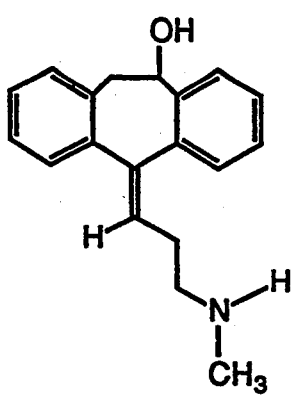
Figure 13:
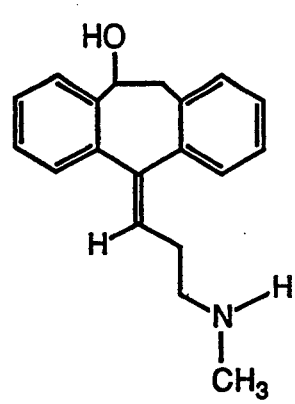

In particular, it was unexpectedly and surprisingly found that for the specific quantification of amitriptyline, the combination of the novel immunogen of Formula III, wherein R is $CH_3$ and which contains a sulfonamide group linked to the aromatic ring [X=(—SO- $_2$—NH—)], and a novel fluorescent tracer of Formula IV, wherein an amide group is linked to the aromatic ring [$W_1Z_1$=(—NH—CO—)], was critical for the specific quantification of amitriptyline as intended by the present invention. This advantageous combination of unique reagents offers an advance in the art for the specific quantification of amitriptyline. For the specific quantification of nortriptyline, the unique combination of reagents comprising the novel immunogen of Formula III, wherein R is H and which contains a sulfonamide group linked to the aromatic ring [X=(—SO$_2$—NH—)], and a novel fluorescent tracer of Formula V, wherein a sulfonamide group is linked to the aromatic ring [$W_2$=—SO$_2$—NH— and $Z_2$=(—CH$_2$—CO—)], was critical for the specific quantification of nortriptyline. This advantageous combination of unique reagents offers an advance in the art for the specific quantification of nortriptyline as intended by the present invention. The performance of the above combinations is illustrated in FIGS. 9 and 10 (amitriptyline) and in FIGS. 11 and 12 (nortriptyline), while correlation with high-performance liquid chromatography (HPLC) is illustrated in FIG. 13 (amitriptyline) and in FIG. 14 (nortriptyline).

When performing a fluorescence polarization immunoassay for the specific quantification of amitriptyline or nortriptyline as described herein, the detectable moiety component of the tracer is a fluorescent moiety such as fluoresceins, aminofluoresceins, carboxyfluoresceins, and the like, preferably aminomethylfluorescein, aminofluorescein, 5-fluoresceinyl, 6-fluoresceinyl, 6-carboxyfluorescein, 5-carboxyfluorescein, thiourea-aminofluorescein, and methoxytriazinolyl-aminofluorescein, and the like fluorescent derivatives. The amount of tracer bound to the antibody varies inversely to the amount of amitriptyline or nortriptyline present in the test sample. Accordingly, the relative, and therefore characteristic, binding affinities of amitriptyline or nortriptyline and the tracer to the antibody binding site, are important parameters of the assay system. Generally, fluorescent polarization techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution. Therefore, within the time frame in which the ligand and tracer compete for binding to the antibody, the tracer and ligand binding rates should yield an appropriate proportion of free and bound tracer with the preservation of important performance parameters such as selectivity, sensitivity, and precision.

When performing a fluorescent polarization immunoassay for the specific quantification of amitriptyline or for the specific quantification of nortriptyline according to the present invention, a test sample suspected of containing amitriptyline or nortriptyline is contacted with antiserum prepared with immunogens according to the present invention in the presence of an appropriately selected fluorescein derivative thereof which is capable of producing a detectable fluorescence polarization response to the presence of antiserum prepared with immunogens according to the present invention. Plane polarized light is then passed through the solution to obtain a fluorescent polarization response and the response is detected as a measure of amount of amitriptyline or nortriptyline present in the test sample.

The amitriptyline and nortriptyline derivatives of the present invention are employed to prepare immunogens by coupling them to conventional carrier materials, and subsequently used to obtain antibodies. The amitriptyline and nortriptyline derivatives are also used to prepare labeled reagents which serve as the detection reagents in immunoassays for quantifying amitriptyline or nortriptyline in a test sample.

The amitriptyline and nortriptyline derivatives of the present invention can be coupled to immunogenic carrier materials by various conventional techniques known in the art where P is an immunogenic carrier material in Formula III. As would be understood by one skilled in the art, the immunogenic carrier material can be selected from any of those conventionally known and, in most instances, will be a protein or polypeptide, although other materials such as carbohydrates, polysaccharides, lipopolysaccharides, poly(amino) acids, nucleic acids, and the like, of sufficient size and immunogenicity can also be employed. Preferably, the immunogenic carrier material is a protein such as bovine serum albumin, keyhole limpet hemocyanin, thyroglobulin, and the like. The immunogens according to the present invention are used to prepare antibodies, both polyclonal and monoclonal, according to methods known in the art for use in an immunoassay system according to the present invention. Generally, a host animal, such as a rabbit, goat, mouse, guinea pig, or horse is injected at one or more of a variety of sites with the immunogen, normally in mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies, and can be stored, for example, at 20° C.

In addition to fluorescence polarization immunoassays, various other immunoassay formats can be followed for the quantification of amitriptyline or nortriptyline according to the present invention. Such immunoassay system formats include, but are not intended to be limited to, competitive, sandwich and immunometric techniques. Generally, such immunoassay systems depend upon the ability of an immunoglobulin, i.e., a whole antibody or fragment thereof, to bind to a specific analyte from a test sample wherein a labeled reagent comprising an antibody of the present invention, or fragment thereof, attached to a label or detectable moiety is employed to determine the extent of binding. Such detectable labels include, but are not intended to be limited to, enzymes, radiolabels, biotin, toxins, drugs, haptens, DNA, RNA, liposomes, chromophores, chemiluminescers, colored particles and colored microparticles, fluorescent compounds such as aminomethylfluorescein, 5-fluoresceinyl, 6-fluoresceinyl, 5-carboxyfluorescein, 6-carboxyfluorescein, aminofluorescein, thioureafluorescein, and methoxytriazinolylaminofluorescein, and the like fluorescent derivatives. As described herein, the test sample can be a naturally occurring or artificially formed liquid, or an extract thereof, and includes, but is not intended to be limited to biological test samples such as whole blood, serum, plasma, urine, feces, saliva, cerebrospinal fluid, brain tissue, and the like. In addition, the test sample can be an extract of a test sample, or any derivative thereof.

Typically, the extent of binding in such immunoassay system formats is determined by the amount of the detectable moiety present in the labeled reagent which either has or has not participated in a binding reaction with the analyte, wherein the amount of the detectable moiety detected and measured can be correlated to the amount of analyte present in the test sample. For example, in a competitive immunoassay system, a substance being measured, often referred to as a ligand, competes with a substance of close structural similarity coupled to a detectable moiety, often referred to as a tracer, for a limited number of binding sites on antibodies specific to the portion or portions of the ligand and tracer with structural similarity, shared with an immunogen employed to produce such antibodies. It is to be understood that since nortriptyline will be present in a test sample as the metabolite of amitriptyline where the drug for treatment is amitriptyline, the amount of amitriptyline and nortriptyline are determined in separate immunoassay systems employing the amitriptyline and nortriptyline derivatives, respectively, of the present invention.

A test kit according to the present invention comprises all of the essential reagents required to perform a desired specific fluorescence polarization immunoassay according to the present invention for the quantification of amitriptyline in a test sample or for the quantification of nortriptyline in a test sample, as described herein. The test kit is presented in a commercially packaged form as a combination of one or more containers holding the necessary reagents, as a composition or admixture where the compatibility of the reagents will allow. Particularly preferred is a test kit for the fluorescent polarization immunoassay quantification of amitriptyline in a test sample or for the fluorescent polarization immunoassay quantification of nortriptyline in a test sample, comprising fluorescent tracer compounds and antibodies produced with the immunogens as described above for the respective quantification of either amitriptyline or nortriptyline. It is to be understood that the test kit can, of course, include other materials as are known in the art and which may be desirable from a commercial user standpoint, such as buffers, diluents, standards, and the like.

The present invention will now be illustrated, but is not intended to be limited by, the following examples. Bold-faced numerals contained in parenthesis refer to the structural formulae as used in the Figures:

EXAMPLE 1

SYNTHESIS OF AMITRIPTYLINE IMMUNOGEN (4)

Solvent abbreviations: $CHCl_3$=chloroform, MeOH=methanol, DMF=dimethylformamide, $CH_2Cl_2$=methylene chloride, $Et_2O$=diethyl ether, EtOAc=ethyl acetate, Hex=hexane, THF=tetrahydrofuran, HOAc=acetic acid.

Amitriptyline hydrochloride (1) (1.00 g, 3.19 mmol) was dissolved in 20 mL $H_2O$, pH adjusted to 12 with 6M NaOH, and extracted with $CHCl_3$ (3×20 mL). The $CHCl_3$ extracts were combined, washed with 20 mL brine, dried over $Na_2SO_4$, and solvent removed in vacuo to afford 815 mg (92%) of the free base as a clear oil. $^1H$ NMR (200 MHz, $CDCl_3$) d 7.3–7.0 (m, 8H), 5.8 (t, 1H), 3.5–2.6 (m, 4H), 2.3–2.2 (m, 4H), 2.2 (s, 6H); mass spec (DCI, $NH_3$) $(M+H)^+$ 278.

Chlorosulfonic acid (0.39 mL, 5.9 mmol) was dissolved in 6.6 mL $CHCl_3$, then added dropwise to a stirred, −15° C. solution of amitriptyline free base (815 mg, 2.94 mmol)in 3.3 mL $CHCl_3$. The resulting yellow solution was then warmed to 50° C., stirred at that temperature for 3 hours, then poured into 50 mL ice water, pH adjusted to 10 with 6 M NaOH, and washed with $CHCl_3$ (15 mL). The aqueous portion was isolated and $H_2O$ removed in vacuo (azeotroped with toluene/MeOH), the resulting white solid triturated with 20 mL MeOH, vacuum filtered, and filtrate solvent removed in vacuo to yield 887 mg (79%) of the desired sulfonic acid sodium salt (2) as a white solid; $^1H$ NMR (200 MHz, $CD_3OD$) d 7.6–7.0 (m, 7H), 5.8 (t, 1H), 3.6–3.2 (m, 4H), 3.1–2.7 (m, 4H), 2.5 (s, 6H); mass spec (FAB) $(M+H)^+$ 358.

The sodium salt (2), (834 mg, 2.20 mmol) was combined with phosphorus pentachloride (916 mg, 4.40 mmol), heated to 90° C., and stirred at that temperature for 25 minutes. After cooling the reaction was diluted with 6 mL $CHCl_3$, poured into 40 mL ice water, treated with 1.2 mL of 6M NaOH, and extracted with $CHCl_3$ (3×40 mL). The $CHCl_3$ extracts were combined, washed with 40 mL brine (saturated aqueous NaCl), dried over $Na_2SO_4$, and solvent removed in vacuo to yield 667 mg (81%) of the desired aryl sulfonyl chloride (3). $^1H$ NMR (200 MHz, $CDCl_3$)d 8.0–7.0 (m, 7H), 5.9 (t, 1H), 3.5–3.2 (m, 2H), 3.2–2.9 (m, 2H), 2.8–2.6 (m, 6H).

The aryl sulfonyl chloride (3) (177 mg, 0.470 mmol) was dissolved in 1.1 mL DMF and added dropwise to a stirred solution of bovine serum albumin (BSA, 400 mg, 0.00588 mmol) dissolved in 6.8 mL of 0.1M sodium phosphate (pH=7.8). After stirring for 3.5 hours the reaction was dialyzed against 2 L of 0.1M sodium phosphate (pH=7.8) for 16 hours, then against $H_2O$ (8×2L). After lyophilization, 389 mg of the desired immunogen (4)was obtained.

EXAMPLE 2

SYNTHESIS OF AMITRIPTYLINE IMMUNOGENS (11), (12) and (13)

Amitriptyline hydrochloride (1) (12.7 g, 40.6 mmol) was dissolved in 250 mL $H_2O$, pH adjusted to 12 with 6 M NaOH, and extracted with $CHCl_3$ (3×250 mL). The $CHCl_3$ extracts were combined, dried over $Na_2SO_4$, and solvent removed in vacuo. The resulting amitriptyline free base (oil) was dissolved in 16 mL $CHCl_3$ and cooled to −15° C. Chlorosulfonic acid (4.8 mL, 72 mmol) in 16 mL $CHCl_3$ was added dropwise, then reaction stirred at 50° C. for 3 hours, cooled to room temperature, poured into 380 mL ice water, pH adjusted to 9–10 with 6M NaOH, washed with 130 mL $CHCl_3$, and $H_2O$ removed in vacuo (azeotroped with toluene/MeOH). The resulting white solid was triturated with 200 mL MeOH, vacuum filtered, and filtrate solvent removed in vacuo to afford a white solid containing at least 4 sulfonic acid isomers of amitriptyline. The E-2, E-3, Z-3 isomers were isolated by preparative reverse phase $C_{18}$ HPLC, eluting with $H_2O$/MeOH/HOAc (50/50/0.4), to yield 1.59 g (11%) of E-2-amitriptyline sulfonic acid (5) as a white solid. $^1H$ NMR (300 MHz, DMSO-d6) d 7.41–7.10 (m, 7H), 5.78 (t, 1H), 3.45–3.13

(m, 4H), 2.95–2.62 (m, 8H), 2.55–2.25 (m, 2H); mass spec (FAB) (M+H)+ 358; 2.35 g (16%) of E-3-amitriptyline sulfonic acid (6) as a white solid. $^1$H NMR (300 MHz, DMSO-d6) d 7.41–7.10 (m, 7H), 5.78 (t, 1H), 3.45–3.13 (m, 4H), 2.95–2.62 (m, 8H), 2.55–2.25 (m, 2H); mass spec (FAB) (M+H)+ 358; and 1.88 g (13%) of Z-2amitriptyline sulfonic acid (7) as a white solid. $^1$H NMR (300 MHz, DMSO-d6) d 7.41–7.10 (m, 7H), 5.78 (t, 1H), 3.45–3.13 (m, 4H), 2.95–2.62 (m, 8H), 2.55–2.25 (m, 2H); mass spec (FAB) (M+)+ 358.

The acid (5) (48 mg, 0.134 mmol) and thionyl chloride (0.8 mL, 11 mmol) were mixed to give a heterogeneous mixture then heated to 70° C. for 1 hour to afford a clear, homogeneous solution from which solvents were removed in vacuo to afford the solid sulfonyl chloride (8).

The sulfonyl chloride (8) was dissolved in 1.5 mL DMF, added to a solution of bovine serum albumin (BSA) (150 mg, 0.00221 mmol)/7 mL phosphate buffer/1.5 mL DMF and stirred 2.5 days. The reaction mixture was dialyzed against 2 L of 0.1M sodium phosphate (pH=7.8) for 16 hours, then against H$_2$O [2 L each, (14 hr, 5 hr, 5 hr, 14 hr, and 6 hr)]. After lyophilization, 140 mg of the desired immunogen (11) was obtained.

The amitriptyline immunogens (12) and (13) were prepared in a similar manner from the acids (6) and (7) respectively.

EXAMPLE 3

SYNTHESIS OF NORTRIPTYLINE IMMUNOGEN (18)

The aryl sulfonyl chloride (3) (5.16 g, 13.7 mmol) was dissolved in 20 mL CHCl$_3$ and added dropwise to a stirred mixture of glycine methyl ester hydrochloride (3.45 g, 27.5 mmol), triethylamine (TEA, 6.7 mL, 48 mmol), and CHCl$_3$ (20 mL). The reaction was stirred for an additional 30 minutes under N$_2$, then vacuum filtered, and filtrate solvent removed in vacuo. The crude product was purified by column chromatography, eluting with CH$_2$Cl$_2$/MeOH (90/10) to afford 1.53 g (26%) of the desired product (14). $^1$H NMR (300 MHz, CDCl$_3$) d 7.09–7.88 (m, 7H), 5.90–6.00 (m, 1H), 3.71–3.80 (m, 2H), 3.59 (s, 3H), 2.65–3.48 (m, 4H), 2.34–2.63 (m, 4H), 2.24 (d, 6H); mass spec (DCI, NH$_3$) (M+H)+429.

The ester (14) (1.42 g, 3.31 mmol) and triethylamine (1.85 mL, 13.3 mmol) were combined in 10 mL CHCl$_3$, then 1.82 mL (13.3 mmol) of 2,2,2-trichloroethylchloroformate was added in a dropwise fashion, while stirring the reaction under N$_2$. After stirring for an additional 3 hours under N$_2$ the reaction was diluted with 60 mL Et$_2$O, washed successively with 0.5M HCl (2×60 mL), H$_2$O (60 mL), and brine (60 mL), then dried over MgSO$_4$, and solvent removed in vacuo. The resulting oil was purified by column chromatography, eluting with EtOAc/Hex (30/70), to yield 1.11 g (44%) of the desired (15a) as a white solid. $^1$H NMR (300 MHz, CDCl$_3$)d 8.03–7.77 (m, 2H), 7.45–7.03 (m, 5H), 6.03–5.88 (m, 1H), 4.85–4.51 (m, 6H), 3.78 (s, 3H), 3.62–3.24 (m, 4H), 3.14–2.73 (m, 5H), 2.60–2.34 (m, 2H); mass spec (FAB) (M−H)+ 764.

The ester (15a) (1.09 g, 1.42 mmol) was dissolved in 9 mL THF, 2.18 g of zinc powder added, 1.8 mL of 1M sodium phosphate (pH=5.5) added, and reaction stirred for 20 hours. The reaction was then vacuum filtered and filtrate solvents removed in vacuo, azeotroping with toluene/MeOH (50/50). The resulting residue was triturated with 25 mL of CHCl$_3$/MeOH (80/20), filtered, and filtrate solvents removed in vacuo to afford 823 mg of the desired nortriptyline derivative (15b). $^1$H NMR (200 MHz, CDCl$_3$-CD$_3$OD)d 8.1–7.0 (m, 7H), 6.2–5.8 (m, 1H), 3.8–3.7 (m, 2H), 3.6 (s, 3H), 3.5–3.2 (m, 4H), 3.1–2.9 (m, 2H), 2.9–2.5 (m, 5H); mass spec (DCI, NH$_3$) (M+H)+ 415.

The free amine (15b) (400 mg, 0.965 mmol) was partially dissolved in 3 mL CHCl$_3$, 0.54 mL (3.9 mmol) of triethylamine (TEA) added, 850 mg (3.9 mmol) of di-tert-butyl dicarbonate (BOC-O-BOC) added, and reaction stirred for 17 hours, under N$_2$. Reaction solvents were then removed in vacuo and the resulting crude oil purified by column chromatography, eluting with EtOAc/Hex (30/70). This product was purified a second time on silica gel (2 mm) preparative TLC plates, eluting with EtOAc/Hex (50/50), to yield 97 mg (20%) of the desired N-BOC protected compound (15c). $^1$H NMR (200 MHz, CDCl$_3$) d 7.8–7.0 (m, 7H), 5.8 (t, 1H), 3.8–3.7 (m, 2H), 3.6 (s, 3H), 3.5–3.2 (m, 4H), 2.9–2.6 (m, 5H), 2.5–2.3 (m, 2H), 1.6–1.2 (m, 9H); mass spec (DCI, NH$_3$) (M+H+NH$_3$)+ 532.

Compound 15c (85 mg, 0.17 mmol) was dissolved in 1.3 mL MeOH, 0.60 mL of 10% NaOH added, and reaction stirred for 30 minutes. The reaction was then diluted with 10 mL H$_2$O, pH adjusted to 4 with 1M HCl, and extracted with CHCl$_3$ (3×10 mL). The CHCl$_3$ extracts were combined, washed with 10 mL brine, dried over Na$_2$SO$_4$, and solvent removed in vacuo to yield 83 mg (100%) of the desired free acid (16). $^1$H NMR (200 MHz, CDCl$_3$) d 7.8–7.0 (m, 7H), 6.0–5.8 (m, 1H), 3.8–3.7 (m, 2H), 3.5–3.2 (m, 4H), 3.2–2.7 (m, 5H), 2.5–2.3 (m, 2H), 1.4 (s, 9H); mass spec (FAB) (M+H)+ 501.

The free acid (16) (59 mg, 0.12 mmol) was dissolved in 0.55 mL DMF, 16 mg (0.14 mmol) of N-hydroxysuccinimide (HOSu) was added, 29 mg (0.14 mmol) of 1,3-dicyclohexylcarbodiimide (DCC) was added, a catalytic amount of 1-hydroxybenzotriazole (HOBT) hydrate was added, and reaction stirred under N$_2$ for 6.5 hours. The reaction was then filtered and filtrate added to a stirred solution of 200 mg (0.0029 mmol) of bovine serum albumin dissolved in 3.4 mL of 0.1M sodium phosphate (pH=7.8) and 0.90 mL DMF. This reaction was stirred for 16 hours, then dialyzed against 2 L of 0.1M sodium phosphate (pH=7.8) for 2 hours, then against H$_2$O (8×2 L). After lyophilization, 218 mg of the desired NBOC immunogen (17) was obtained.

To 200 mg of the N-BOC immunogen (17) was added 10 mL of CH$_2$Cl$_2$, followed by 10 mL of trifluoroacetic acid (TFA). After stirring for 5 minutes, solvents were removed in vacuo, then residue redissolved in 50 mL of 0.1M sodium phosphate (pH=7.8), and the resulting cloudy solution was dialyzed against 2 L of 0.1M sodium phosphate (pH=7.8) for 16 hours, then against H$_2$O (7×2 L). After lyophilization, 131 mg of the desired nortriptyline immunogen (18) was obtained.

EXAMPLE 4

SYNTHESIS OF NORTRIPTYLINE IMMUNOGENS (22), (23) and (24)

The sulfonyl chloride (8) was dissolved in 30 mL CHCl$_3$ and added to a stirred mixture of glycine methyl ester hydrochloride (3.77 g, 30.0 mmol) and triethylamine (6.3 mL, 45 mmol) in 30 mL CHCl$_3$. Another 2.1 mL (15 mmol) of triethylamine was added, and reaction allowed to stir for 3 days, under N$_2$. The reaction was then poured into 300 mL CHCl₃, washed successively with 0.5M K₂CO₃ (2×100 mL) and brine (100 mL), dried over Na₂SO₄, and solvent removed *in vacuo*. The resulting crude residue was purified by column chromatography, eluting with CH₂Cl₂/MeOH (85/15), to yield 4.08 g (73%) of the desired ester (19). ¹H NMR (300 MHz, CDCl₃) d 7.59 (d, 1H), 7.53 (s, 1H), 7.41 (d, 1H), 7.27–7.10 (m, 4H), 5.93 (t, 1H), 3.72 (s, 2H), 3.58 (s, 3H), 3.48–2.70 (m, 4H), 2.48–2.25 (m, 4H), 2.19 (s, 6H); mass spec (FAB) (M+H)+ 429.

2,2,2-Trichloroethylchloroformate (5.2 mL, 38 mmol) in 9 mL CHCl₃ was added, under N₂, in a dropwise fashion, to a stirred, 0° C. solution of methyl ester (19) (4.03 g, 9.40 mmol) and triethylamine (5.2 mL, 38 mmol) in 30 mL CHCl₃. The reaction was then stirred at room temperature for 4.5 hours, then diluted with 180 mL Et₂O, washed successively with 0.5 M HCl (2×180 mL), H₂O (180 mL), and brine (180 mL), dried over MgSO₄, and solvent removed *in vacuo*. The resulting residue was purified by silica gel column chromatography, eluting with EtOAc/Hex (30/70), to afford 3.21 g (45%) of the desired protected amine (20a). ¹H NMR (300 MHz, CDCl₃) d 7.90–7.75 (m, 2H), 7.41 (d, 1H), 7.30–7.14 (m, 3H), 7.14–7.05 (m, 1H), 5.97–5.85 (m, 1H), 4.80–4.50 (m, 6H), 3.77 (s, 3H), 3.65–3.20 (m, 4H), 3.10–2.70 (m, 5H), 2.60–2.30 (m, 2H); mass spec (FAB) (M+H)+ 765.

The ester (20a) (3.17 g, 4.14 mmol) was dissolved in 27 mL THF, 6.34 g of zinc powder added, 5.4 mL of 1M sodium phosphate (pH=5.5) added, and reaction stirred overnight. The reaction was then filtered and filtrate solvent removed *in vacuo* (azeotroped with toluene/MeOH). The crude residue was purified by silica gel column chromatography, eluting first with THF/MeOH/NH₄OH (85/15/0.4) until two major impurities were removed, then with THF/MeOH/NH₄OH (75/25/0.4), to yield 1.40 g (81%) of the desired secondary amine (20b). ¹H NMR (200 MHz, CDCl₃-CD₃OD) d 7.7–7.4 (m, 3H), 7.3–7.1 (m, 4H), 5.9 (t, 1H), 3.7 (s, 2H), 3.6 (s, 3H), 3.5–3.3 (m, 2H), 3.2–2.8 (m, 4H), 2.7–2.4 (m, 5H); mass spec (FAB) (M+H)+ 415.

The amine (20b) d (1.373 g, 3.31 mmol) was dissolved in 11 mL DMF, 795 mg (3.64 mmol) of di-tert-butyl dicarbonate was added, 0.55 mL (3.9 mmol) of triethylamine was added, and reaction stirred under N₂ for 16 hours. Solvent was then removed *in vacuo* and residue purified by silica gel column chromatography, eluting with EtOAc/Hex (50/50) to afford 1.01 g (59%) of the desired BOC-protected amine (20c). ¹H NMR (200 MHz, CDCl₃) d 7.7–7.4 (m, 3H), 7.3–7.1 (m, 4H), 5.9 (t, 1H), 3.7 (d, 2H), 3.6 (s, 3H), 3.5–3.2 (m, 2H), 3.1–2.8 (m, 2H), 2.7 (s, 3H), 2.4–2.3 (m, 2H), 1.5–1.2 (m, 9H); mass spec (DCl, NH₃) (M+NH₄)+ 532.

The protected amine (20c) (983 mg, 1.91 mmol) was dissolved in 18.3 mL MeOH, 6.1 mL (15 mmol) of 10% aqueous NaOH was added, and reaction stirred for 20 minutes. The reaction was then diluted with 75 mL H₂O, pH adjusted to 3–4 with 1M HCl, and extracted with CHCl₃ (3×75 mL). The CHCl₃ extracts were combined, washed with 75 mL brine, dried over Na₂SO₄, and solvent removed *in vacuo* to yield 955 mg (100%) of the desired acid (21). ¹H NMR (200 MHz, CDCl₃) d 7.7–7.4 (m, 3H), 7.3–7.0 (m, 4H), 5.9 (t, 1H), 3.7 (d, 2H), 3.5–3.2 (m, 4H), 3.2–2.8 (m, 2H), 2.7 (s, 3H), 2.5–2.3 (m, 2H), 1.5–1.2 (m, 9H); mass spec (FAB) (M+H+Na)+ 523.

The acid (21) (52 mg, 0.10 mmol) was dissolved in 0.50 mL DMF, 14 mg (0.12 mmol) of N-hydroxysuccinimide (HOSu) was added, 25 mg (0.12 mmol) of 1,3-dicyclohexylcarbodiimide (DCC) was added, a catalytic amount of 1-hydroxybenzotriazole (HOBT) hydrate was added, and reaction stirred under N₂ for 5 hours. The reaction was then filtered and filtrate added to a stirred solution of 171 mg (0.0026 mmol) of bovine serum albumin dissolved in 3.5 mL of 0.1M sodium phosphate (pH=7.8) and 0.9 mL DMF. This reaction was stirred for 16 hours, then dialyzed against 2 L of 0.1M sodium phosphate (pH=7.8) for 2 hours, then against H₂O [2 L each (14 hr, 4 hr, 4 hr, 14 hr, 6 hr)]. After lyophilization, 195 mg of the desired N-BOC immunogen was obtained.

The intermediate N-BOC immunogen (186 mg) was placed in 10 mL of CH₂Cl₂, followed by 10 mL of trifluoroacetic acid (TFA). After stirring for 5 minutes, solvents were removed in vacuo, then residue redissolved in 50 mL of 0.1M sodium phosphate (pH=7.8), and the resulting cloudy solution was dialyzed against 2 L of 0.1M sodium phosphate (pH=7.8) for 16 hours, then against H₂O [2 L each (14 hr, 4 hr, 5 hr, 14 hr, 6 hr)]. After lyophilization, 118 mg of the desired nortriptyline immunogen (22) was obtained.

The nortriptyline immunogens (23) and (24) were prepared in a similar manner from the sulfonyl chlorides (9) and (10) respectively.

EXAMPLE 5

SYNTHESIS OF AMITRIPTYLINE TRACER (27)

Imipramine hydrochloride (25) (2.21 g, 6.97 mmol) was dissolved in 35 mL H₂O, made basic with 6M NaOH, and extracted with CHCl₃ (3×35 mL). The CHCl₃ extracts were combined, washed with 35 mL brine, dried over Na₂SO₄, and solvent removed *in vacuo* to afford 1.95 g of the desired imipramine free base. ¹H NMR (200 MHz, CDCl₃) d 7.2–7.1 (m, 6H), 7.0–6.8 (m, 2H), 3.8 (t, 2H), 3.2 (s, 4H), 2.3 (t, 2H), 2.1 (s, 6H), 1.7 (p, 2H).

Imipramine (26a, 1.925 g, 6.87 mmol) was dissolved in 32 mL acetic acid and cooled to 18° C. Conc. nitric acid (0.79 mL, 13 mmol) in 1.1 mL acetic acid was added dropwise, with stirring, keeping reaction at 17°–18° C., then reaction stirred at that temperature for an additional 20 minutes. The reaction was then poured into 130 mL of 0.15M HCl and washed with Et₂O (2×85 mL), then pH adjusted to 13 with conc. NaOH and extracted with CHCl₃ (4×100 mL). The CHCl₃ extracts were combined, washed with 85 mL brine, dried over Na₂SO₄, and solvent removed *in vacuo*. The residue was purified by column chromatography, eluting with THF/Hex/NH₄OH (70/30/0.4) to yield 1.145 g (51%) of the desired 2-nitroimipramine (26b) as a red oil. ¹H NMR (200 MHz, CDCl₃) d 8.0–7.9 (m, 2H), 7.3–7.0 (m, 5H), 3.9 (t, 2H), 3.2 (s, 4H), 2.3 (t, 2H), 2.1 (s, 6H), 1.7 (p, 2H); mass spec (FAB) (M+H)+ 326.

2-Nitroimipramine (26b, 552 mg, 1.70 mmol) was dissolved in 20 mL absolute EtOH, 55 mg of 10% palladium on carbon added, and reaction stirred under H₂ (balloon pressure) for 3.5 hours. The reaction was then vacuum filtered through celite, and filtrate solvents were removed *in vacuo* to afford 499 mg (99%) of the desired 2-aminoimipramine (26c) as a pale yellow oil. ¹H NMR (200 MHz, CDCl₃) d 7.2–7.0 (m, 3H), 6.9–6.8 (m, 2H), 6.5–6.4 (m, 2H), 3.7 (t, 2H), 3.2–3.0 (m, 4H), 2.3 (t, 2H), 2.1 (s, 6H), 1.7 (p, 2H); mass spec (FAB) (M+H)+ 296.

6-Carboxyfluorescein (1.00 g, 2.66 mmol) was dissolved in 8 mL DMF, 306 mg (2.66 mmol) of N-hydroxysuccinimide (HOSu) was added, 549 mg (2.66 mmol) of 1,3-dicyclohexylcarbodiimide (DCC) was added, and the reaction stirred for 17 hours, under $N_2$, in the dark. The reaction was then vacuum filtered, filtrate combined with 784 mg (2.65 mmol) of 2-aminoimipramine (26c), 0.56 mL (4.0 mmol) of triethylamine, and 4.0 mL DMF, and reaction allowed to stir 4 days under $N_2$, in the dark. Reaction solvents were removed in vacuo and residue purified on reverse phase $C_{18}$ preparative (1 mm) TLC plates, eluting with $H_2O$/THF/HOAc (40/60/0.4) followed by preparative HPLC on a Waters mbondapak $C_{18}$ column (19 mm × 150 mm), eluting with $H_2O$/THF/HOAc (35/65/0.4) at a flow rate of 7.0 mL/minute to yield 410 mg (24%) of the desired tracer (27) as an orange powder; mass spec (FAB) $(M+H)^+$ 654.

EXAMPLE 6

SYNTHESIS OF NORTRIPTYLINE TRACER (30)

The acid (21) (466 mg, 0.931 mmol) was dissolved in 5 mL DMF, 259 mg (1.02 mmol) of 2-ethyl-5-phenylisoxazolium-3'-sulfonate (Woodward's reagent K) added, 0.195 mL (1.40 mmol) of triethylamine added, and reaction stirred for 40 minutes under $N_2$. Then 370 mg (0.931 mmol) of aminomethylfluorescein hydrochloride was added, followed by 0.650 mL (4.7 mmol) of triethylamine, and reaction stirred for 17 hours, under $N_2$, in the dark. Solvents were then removed in vacuo and residue purified by silica gel column chromatography, eluting with $CH_2Cl_2$/MeOH (95/5) until a major faster-eluting impurity was removed, then with $CH_2Cl_2$/MeOH (80/20), to afford 379 mg (48%) of the desired N-BOC protected nortriptyline tracer (28) as an orange solid; mass spec (FAB) $(M+H)^+ 844$.

The N-BOC nortriptyline tracer (28) (362 mg, 0.429 mmol) was stirred in 4.3 mL $CH_2Cl_2$, 4.3 mL of trifluoroacetic acid added, reaction stirred for 5 minutes, then solvent removed in vacuo. The residue was redissolved in $CH_2Cl_2$/MeOH (50/50) (10 mL), pH adjusted to 7 with triethylamine, and solvent removed in vacuo. The resulting crude product was purified on reverse phase $C_{18}$ preparative (1 mm) TLC plates, eluting with $H_2O$/MeOH/HOAc (15/85/0.4), to yield 388 mg of the desired nortriptyline tracer (29) as an orange solid; mass spec (FAB) $(M+H)^+ 744$.

EXAMPLE 7

SYNTHESIS OF AMITRIPTYLINE TRACER (30)

The sulfonyl chloride (3) (84 mg, 0.23 mmol) was dissolved in 0.5 mL DMF/186 mL triethylamine (1.36 mmol), aminomethylfluorescein added (30 mg, 0.075 mmol), and reaction stirred 3.5 hours under nitrogen. The solvents were removed in vacuo to give 148 mg crude orange solid which was purified on C-18 preparative tlc plates to afford 14.1 mg of the desired tracer (30); mass spec (FAB) $(M+H)^+ 701$.

EXAMPLE 8

SYNTHESIS OF NORTRIPTYLINE TRACER (31)

Triethylamine (0.21 mL, 1.52 mmol) was added to a solution of N'-BOC protected carboxylic acid (21) (25 mg, 0.050 mmol)/Woodward's K (14 mg, 0.055 mmol)/0.5 mL DMF, stirred 35 min and aminomethylfluorescein (20 mg, 0.050 mmol) was added along with triethylamine (0.21 mL, 1.52 mmol). The reaction was stirred 18 hours in the dark under nitrogen and solvents removed/n vacuo to give an orange solid which was purified on preparative tlc plates to afford 21 mg of the desired N'-BOC protected intermediate; mass spec (FAB) $(M)^+ 844$.

The N'-BOC protected intermediate (20 mg, 0.024 mmol) was dissolved in 0.50 mL $CH_2Cl_2$, trifluoroacetic acid (0.50 mL) was added, reaction was stired for 5 minutes, and the resulting solution was stripped to dryness. The solid was dissolved in 0.5 mL $CH_2Cl_2$ and 0.5 mL triethylamine then solvents removed/n vacuo to afford an orange solid which was purified on C-18 preparative tlc plates to afford 9.0 mg of the desired tracer (31); mass spec (FAB) $(M+H)^+ 744$.

EXAMPLE 9

ANTISERA PRODUCTION

Rabbits were initially immunized with 1 mg of immunogen and subsequently boosted with 0.5 mg of the immunogen until the response was mature (~12–15 weeks), after which the animals were boosted with 0.2 mg of the immunogen every 4 weeks. The animals were bled at 2 weeks and the bleeds were titrated to select antisera collections demonstrating adequate binding and displacement at a reasonable dilution. A typical pool for amitriptyline is diluted 1 to 45, has a binding of about 210 millipolarization units (mP) and a displacement of about 95 mP's with an amitriptyline solution containing 100 ng amitriptyline per milliliter; for nortriptyline a typical pool is diluted 1 to 250, has a binding of about 210 millipolarization units and a displacement of about 120 mP's with a nortriptyline solution containing 100 ng nortriptyline per milliliter.

EXAMPLE 10

FLUORESCENCE POLARIZATION IMMUNOASSAY FOR AMITRIPTYLINE

Antisera was prepared by combining sera from 6 rabbits that had been immunized with the amitriptyline immunogen (4) as described in example 1. Individual titers among animals varied no more than 30% and all animals exhibited a mature immune response (6 months or greater on a single immunogen). The immunogen used was obtained from at least two separate synthetic preparations and gave equivalent response as judged by titer, avidity (curve characteristics), and cross-reactivity to nortriptyline (<10% at 50% deflection). The raw antisera were mixed and diluted into a buffer consisting of 0.100M glycylglycine, adjusted to pH 4.5 with 70% phosphoric acid. During the course of the assay the antisera was diluted in the TDx system with TDx system reagent buffer to a final concentration 1:4,000.

The fluorescent tracer (27) described in example 5 was prepared by diluting the dry reagent in a solution consisting of 25% dimethylformamide, 25% glycerol, and 50% distilled water in which was dissolved sufficient sodium chloride, and sodium thiosulfate, to result in concentrations of 1.0%, and 0.1% respectively. This tracer reagent stock solution was then diluted to a concentration of ~82 nM in the same diluent matrix for use in the assay. During the course of the assay, this diluted tracer preparation is further diluted with TDx system reagent buffer to a final concentration of ~1.0 nM.

Each test sample was prepared for analysis by means of a off-line multistep biphasic extraction procedure. To a 1.25 mL polypropylene test tube 0.200 mL of sample was added. This test sample was then rendered basic by the addition of 0.100 mL of 0.25N sodium hydroxide and 0.020 mL of isoamylalcohol. This solution was mixed and allowed to stand at room temperature for 5 minutes. At the end of this period, 0.500 mL of n-decane was added to the sample followed by vortex mixing for 1.0 minute. After vortexing the sample was centrifuged for 5.0 minutes at ~8,000×g. At the end of this 5.0 minute centrifugation, 0.200 mL of the supernatant (upper phase) was removed to a second 1.25 mL polypropylene test tube containing 0.200 mL of 0.100M glyclyglycine buffer (pH 3)/acetonitrile solution in a proportion of 9:1, respectively. At that point 0.040 mL of pretreatment solution (Z reagent = 10 ug/mL solution of aqueous Chloramine-T) as described in U.S. patent application, U.S. Ser. No. 627,282 filed Dec. 14, 1990. The solution was vortex mixed for 1.0 minute and between 50 and 0.100 mL of the lower phase from the second tube transferred to the sample well on an Abbott TDx ® analyzer.

The sample was run according to the standard protocol on the TDx analyzer in which the sample volume of 0.020 mL was combined with 0.025 mL of diluted antisera and 0.025 mL of diluted fluorescent tracer. The results at the termination of the assay run are expressed in millipolarization units (mP). The millipolarization units are automatically interpolated from a stored standard curve (FIG. 8) and expressed as concentration (ng/mL). Since the sample preparation procedure for the assay incorporates a 3-fold dilution of the sample, the gravimetric concentration of the calibrators from which the stored curve is constructed by a weighted four parameter curve fit are one third the expressed nominal concentration. The calibrators are prepared by gravimetric dilution in a buffer composed of 0.100M glycylglycine, pH 3. They are introduced into the TDx analyzer directly, without off-line sample treatment (biphasic extraction).

EXAMPLE 11

FLUORESCENCE POLARIZATION IMMUNOASSAY FOR NORTRIPTYLINE

Antisera was prepared by combining sera from 6 rabbits that had been immunized with the nortriptyline immunogen (18) as described in example 3 Individual titers among animals varied no more than 30% and all animals exhibited a mature immune response (6 months or greater on a single immunogen). The immunogen used was obtained from at least two separate synthetic preparations and gave equivalent response as judged by titer, avidity (curve characteristics), and crossreactivity to amitriptyline (<10% at 50% deflection). The raw antisera were mixed and diluted into a buffer consisting of 0.100M phosphate buffered saline, adjusted to pH 7.0. During the course of the assay the antisera was diluted in the TDx system with TDx system reagent buffer to a final concentration 1:16,000.

The nortriptyline fluorescent tracer (29) described in example 6 was prepared by diluting the dry reagent in a solution consisting of 25% dimethylformamide, 25% glycerol, and 50% distilled water in which was dissolved sufficient sodium chloride, and sodium thiosulfate, to result in concentrations of 1.0%, and 0.1% respectively. This tracer reagent stock solution was then diluted to a concentration of ~82 nM in the same diluent matrix for use in the assay. During the course of the assay, this diluted tracer preparation is further diluted with TDx system reagent buffer to a final concentration of ~1.0 nM.

Each test sample was prepared for analysis by means of a off-line multistep biphasic extraction procedure. To a 1.25 mL polypropylene test tube 0.200 mL of sample was added. This test sample was then rendered basic by the addition of 0.100 mL of 0.25N sodium hydroxide and 0.020 mL of isoamylalcohol. This solution was mixed and allowed to stand at room temperature for 5 minutes. At the end of this period, 0.500 mL of n-decane was added to the sample followed by vortex mixing for 1.0 minute. After vortexing the sample was centrifuged for 5.0 minutes at ~8,000×g. At the end of this 5.0 minute centrifugation, 0.200 mL of the supernatant (upper phase) was removed to a second 1.25 mL polypropylene test tube containing 0.200 mL of 0.100M glyclyglycine buffer (pH 3)/acetonitrile solution in a proportion of 9:1, respectively.. At that point 0.040 mL of pretreatment solution (Z reagent = 10 ug/mL solution of aqueous Chloramine-T) as described in U.S. patent application, U.S. Ser. No. 627,282 filed Dec. 14, 1990. The solution was vortex mixed for 1.0 minute and between 50 and 0.100 mL of the lower phase from the second tube was transferred to the sample well on an Abbott TDx ® analyzer.

The sample was run according to the standard protocol on the TDx analyzer in which the sample volume of 0.015 mL was combined with 0.025 mL of diluted antisera and 0.025 mL of diluted fluorescent tracer. The results at the termination of the assay run are expressed in millipolarization units (mP). The millipolarization units are automatically interpolated from a stored standard curve (FIG. 9) and expressed as concentration (ng/mL). Since the sample preparation procedure for the assay incorporates a 3-fold dilution of the sample, the gravimetric concentration of the calibrators from which the stored curve is constructed by a weighted four parameter curve fit are one third the expressed nominal concentration. The calibrators are prepared by gravimetric dilution in a buffer composed of 0.100M glycylglycine, pH 3. They are introduced into the TDx analyzer directly, without off line sample treatment (biphasic extraction).

EXAMPLE 12

EFFECT OF STRUCTURAL MODIFICATION OF TRACER IN AMITRIPTYLINE ASSAY

Figure 7A:
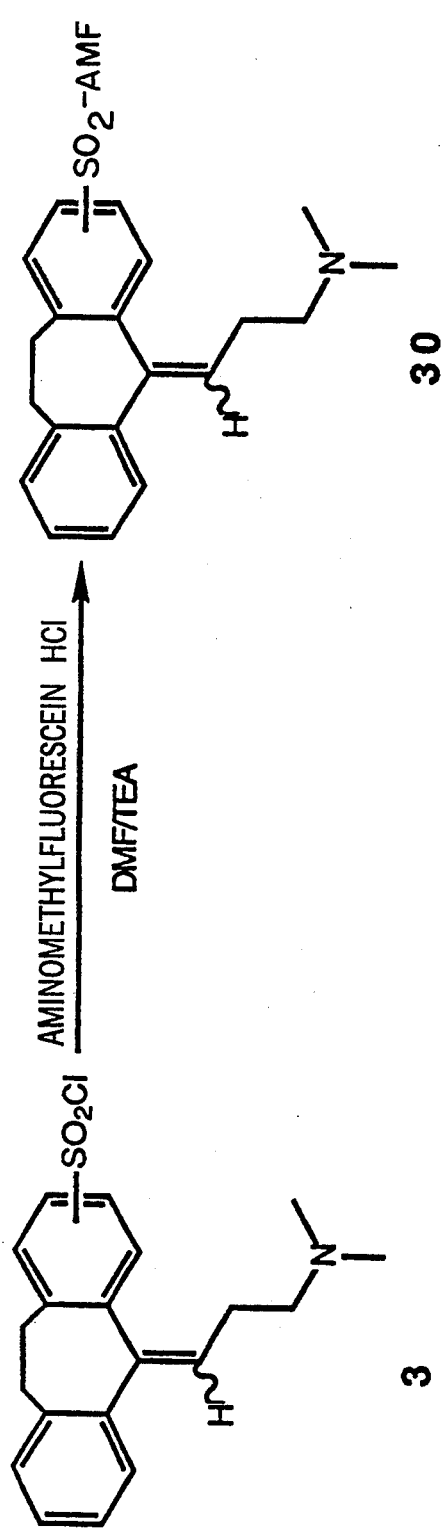
FIGS. 7A and 7B illustrate the synthetic pathway to an alternate amitrip-tyline fluorescent tracer and an alternate nortriptyline fluorescent tracer according to the method of the present invention.
Figure 7A:
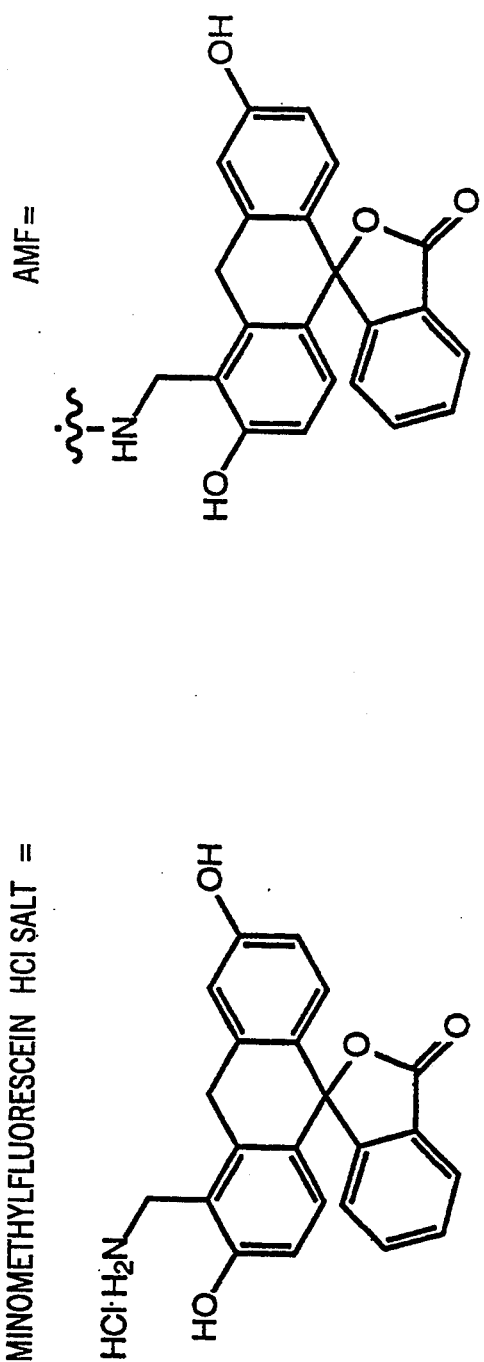
Figure 7B:
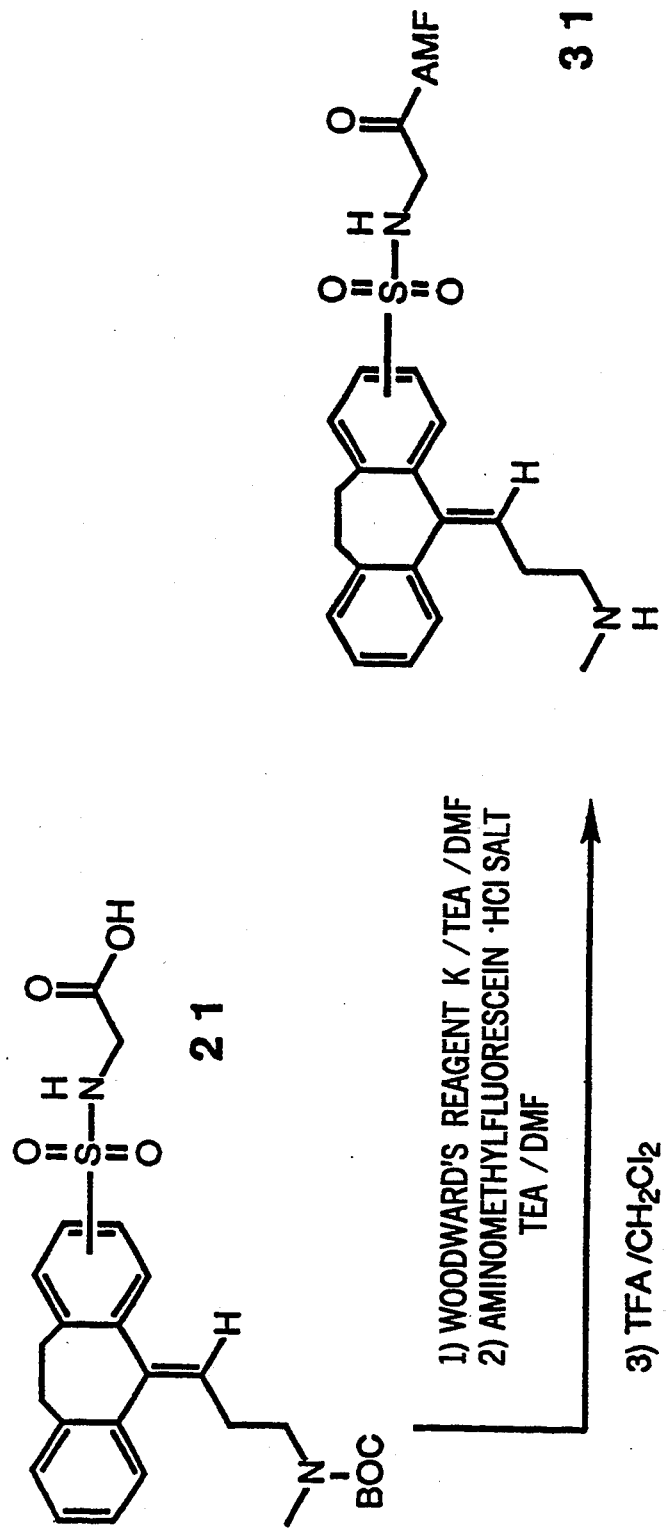
Figure 8:
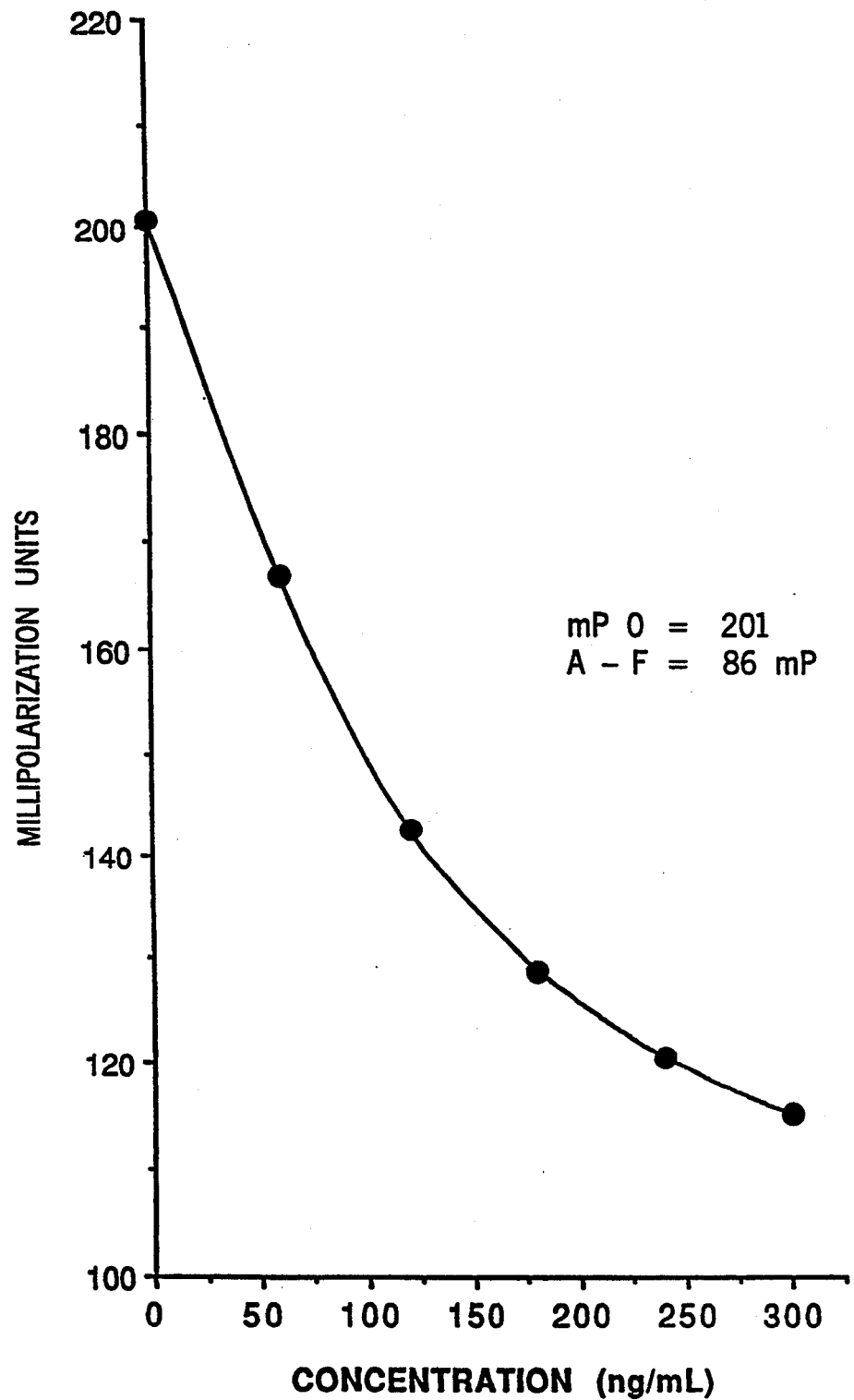
FIG. 8 is a graph which illustrates an amitriptyline calibration curve on the Abbott TDx ® analyzer.

Modification of the fluorescent tracer structure from an amitriptyline sulfonamide as shown in FIG. 7 to an amide as shown in FIG. 5 had a dramatic effect on assay characteristics. Calibration curves were generated from six known concentrations using the two fluorescent tracers (27) and (30). In the case of the amitriptyline derived tracer (30), cross-reactivity to amitriptyline metabolites were in excess of the desired assay performance, see FIG. 11. When the tracer (27) was used, excellent displacement of the tracer by amitriptyline from the antibody-tracer complex occurs as well as a dramatic decrease in cross-reactivity, see FIGS. 10 and 11. These findings illustrate a preferred embodiment of the invention for a specific amitriptyline assay.

EXAMPLE 13

EFFECT OF STRUCTURAL MODIFICATION OF TRACER IN NORTRIPTYLINE ASSAY

Modification of the fluorescent tracer structure from a mixed nortriptyline sulfonamide as shown in FIG. 7 to an isomerically pure sulfonamide as shown in FIG. 6 had a dramatic effect on assay characteristics. Calibration curves were generated from six known concentrations using the two fluorescent tracers (29) and (31). In the case of the amitriptyline derived tracer (31), cross-reactivity to amitriptyline metabolites were in excess of the desired assay performance, see FIG. 13. When the tracer (29) is used, excellent displacement of the tracer by nortriptyline from the antibody-tracer complex occurs as well as a dramatic decrease in cross-reactivity, see FIGS. 12 and 13. These findings illustrate a preferred embodiment of the invention for a specific nortriptyline assay.

EXAMPLE 14

COMPARATIVE ANALYSIS OF AMITRIPTYLINE TDx ASSAY VS. HPLC

The relative accuracy of the Amitriptyline TDx assay was determined by correlation with HPLC using patient sample extracts. The extracts for HPLC analysis were prepared as described below and the tricyclic antidepressants trimipramine and Z-desmethyldoxepin were used, each at a concentation of 4 ug/mL in acetonitrile, as internal standards.

1. Pipette 1.0 mL of patient standard into a 16×125 silylated tube fitted with a teflon screw cap. Remove the appropriate standard calibration curve frozen aliquots from the freezer and allow to thaw. Add 0.75 mL of acetonitrile containing the internal standard to each tube.

2. Add 1.0 mL of 0.25N NaOH followed by 0.200 mL 0f isoamyl alcohol, vortex vigorously, and allow the tubes to stand for 5.0 min.

3. Into each tube pipette 10.0 mL of n-heptane and tightly secure the cap of each tube. Shake the heptane/plasma biphasic mixture vigorously for 1.0 hour.

4. Remove the tubes from the shaker and transfer to the centrifuge. Centrifuge the heptane/plasma mixtures for 30 min at at least 2000×gravity(g) to clarify the layer.

5. Remove the tubes from the centrifuge and transfer the heptane upper layer to another silylated tube of the same description containing 1.0 mL of 0.1M, pH 3 glycylglycine buffer. Cap these tubes and shake vigorously for 1.0 hour.

6. Remove the tubes from the shaker and transfer to a centrifuge. Centrifuge the biphasic glycyl-glycine/heptane mixture for 30 min. at at least 2000×g.

7. Remove the tubes from the centrifuge, uncap and aspirate or pipette off the heptane upper layer and discard it.

8. Add 2.0 mL of 0.25N NaOH to each remaining glycylglycine lower phase. Add 5.0 mL of n-pentane to each aqueous extract, cap the tubes and shake for 1.0 hour.

9. Remove the tubes from the shaker and transfer to a centrifuge. Centrifuge the pentane/aqueous mixture at 200×g for 30 min.

10. Remove the tubes from the centrifuge and transfer the pentane upper layer to a 16×100 silylated conical screw top test tube. Place the caps on the test tubes tightly and unscrew ¼ turn. Place the tubes in a warm sand bath, transfer the sand bath containing the tubes to a vacuum desicator cabinet and apply the vacuum. Approximately 25-30 min is required for the pentane to evaporate.

11. Remove the tubes in the sand bath from the desicator and pipette into each tube 1.0 mL of pentane, recap and vortex each tube briefly. Open the caps ¼ turn and return the tubes to the desicator and reapply the vacuum for 10-15 min. until the pentane has evaporated.

12. Remove the dry tubes from the desicator and pipette in 0.070 mL of HPLC mobile phase. Vortex each tube for approx. 30 sec taking care to wet the tube sides.

13. Transfer the tubes to a centrifuge and centrifuge at 200 ×g for 2-3 min.

14. Remove the tubes from the centrifuge and transfer the entire contents to the WISP autocarousel sample cuvettes. The injection volume is set at 0.050 mL per injection onto a 10 cm.×0.6 cm. column packed with 3 micron silica with an 80 Angstrom pore size. The chromatographic mobile phase consisted of a mixture of 80 parts 0.025M dibasic sodium phosphate adusted to pH 3 with concentrated phosphoric acid/20 parts acetonitrile/0.021M n-nonylamine(pH range=7.4-7.8). The analytical column is equipped with a dry packed guard column containing 40 micron pellicular silica. The solvent flow rate was 1.6 mL/min.

Figure 14:
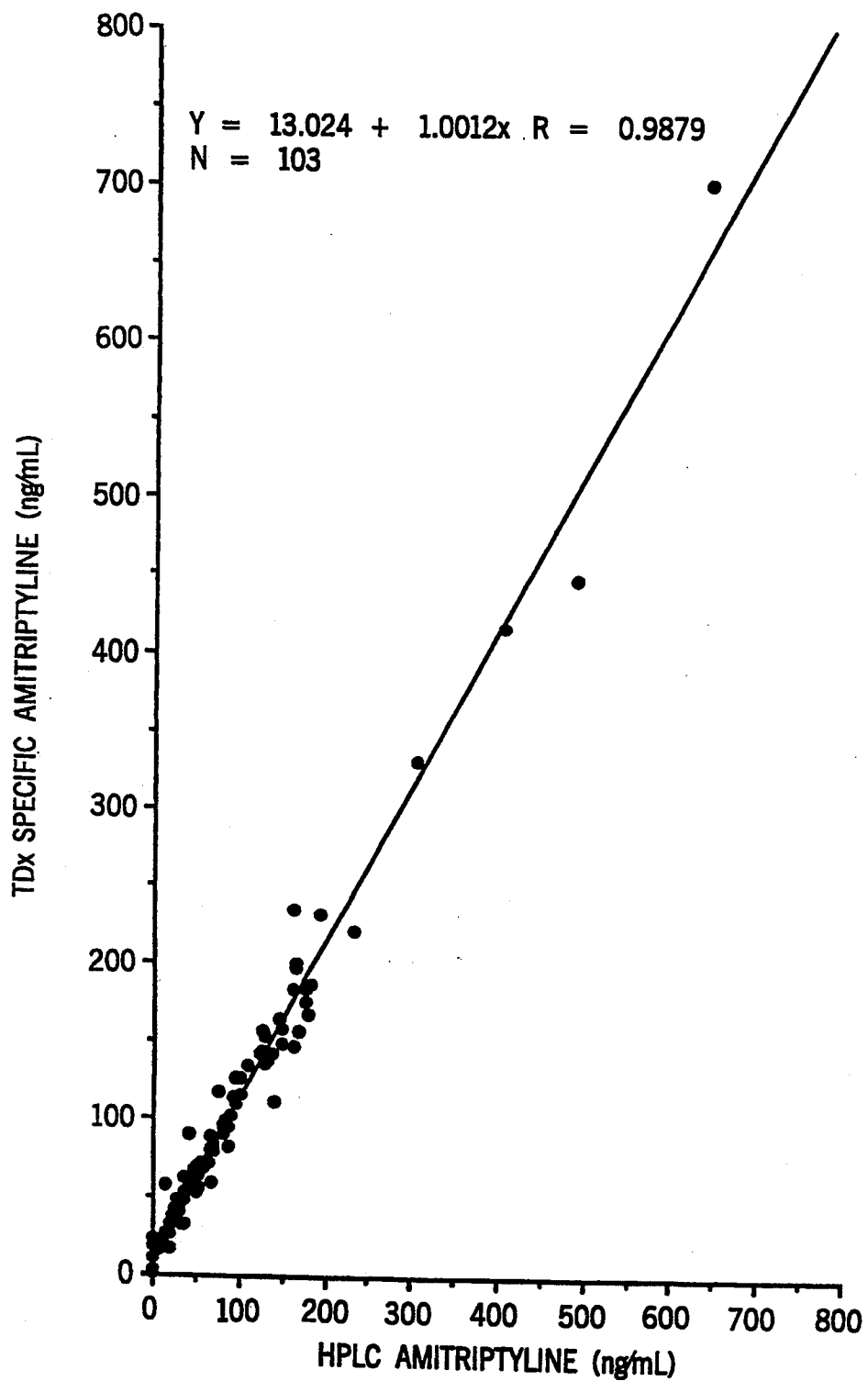
FIG. 14 is a graph which illustrates the accuracy of the method of fluorescence polarization immunoassay for the specific quantification of amitriptyline of the present invention compared to high performance liquid chromatography.

Linear regression analysis showed good correlation between the Amitriptyline TDx Assay and the HPLC assay (N=103, R=0.9879, S=1.0012). The results are shown in FIG. 14.

EXAMPLE 15

COMPARATIVE ANALYSIS Of NORTRIPTYLINE TDx ASSAY VS. HPLC

Figure 15:
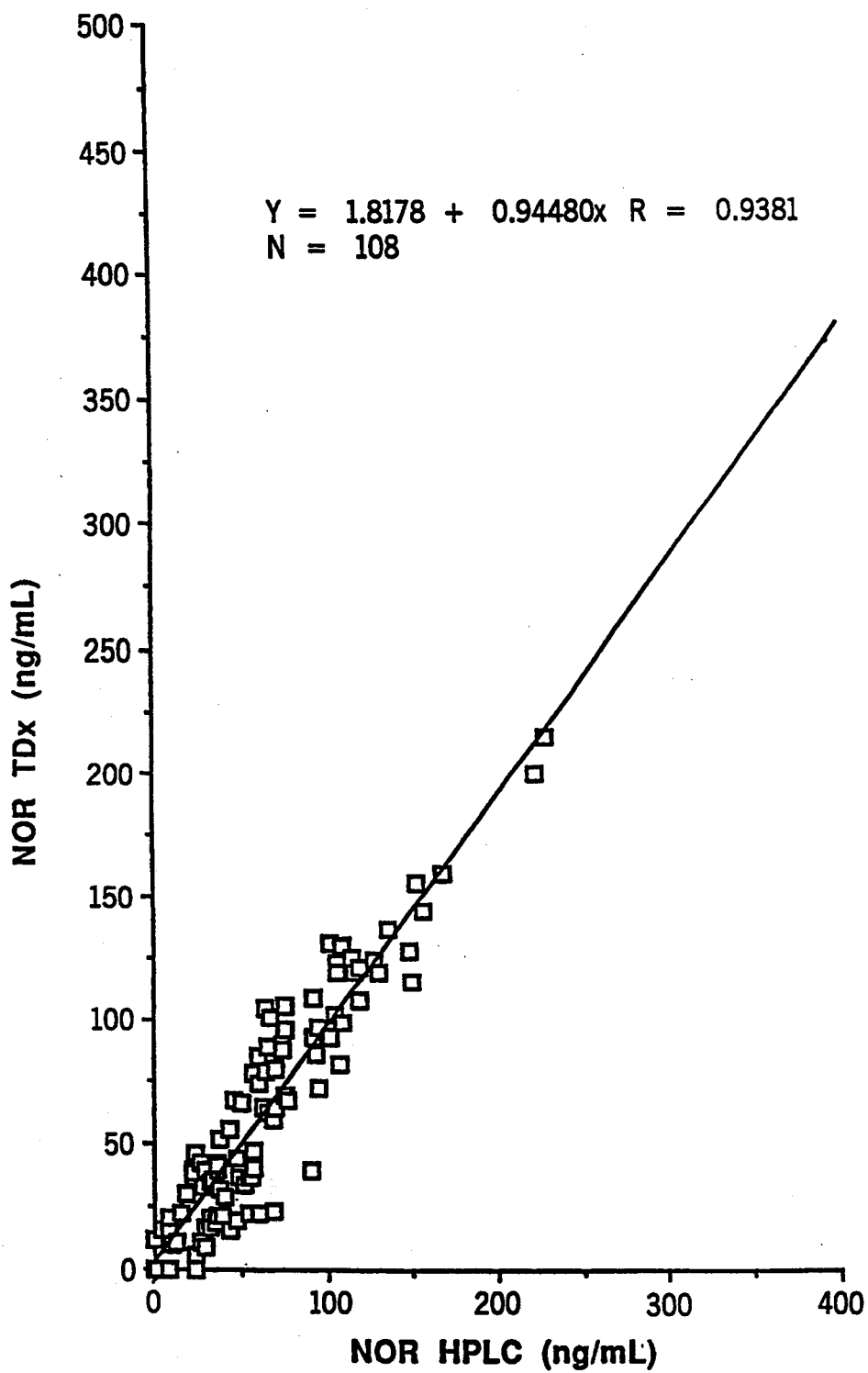
FIG. 15 is a graph which illustrates the accuracy of the method of fluorescence polarization immunoassay for the specific quantification of nortriptyline of the present invention compared to high performance liquid chromatography.

The relative accuracy of the Nortriptyline TDx assay was determined by correlation with HPLC using patient sample extracts. The extracts for HPLC analysis were prepared and the chromatographic conditions used were the same as described above. Linear regression analysis showed good correlation between the Nortriptyline TDx Assay and the HPLC assay (N=108, R=0.9381, S=0.9448). The results are shown in FIG. 15.

We claim:

1. An immunoassay method for the quantification of amitriptyline in a test sample, said method comprising the steps of:
   (a) contacting said test sample with a labeled reagent and an antibody reagent to form a reaction solution therewith, said antibody reagent comprising antibodies which are capable of binding to amitriptyline, wherein
       (i) said antibodies are produced with an immunogen of the formula:

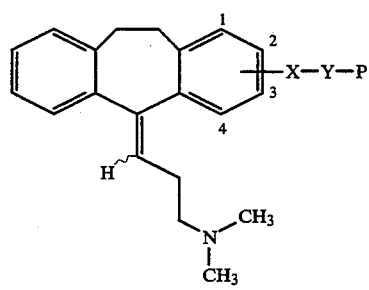

wherein
X is —SO$_2$—NH— linked to the aromatic ring in the 2 or 3 position, Y is a linking group comprising from 0 to 6 carbon atoms, and P is an immunogenic carrier material; and (ii) said labeled reagent for the specific quantification of amitriptyline is:

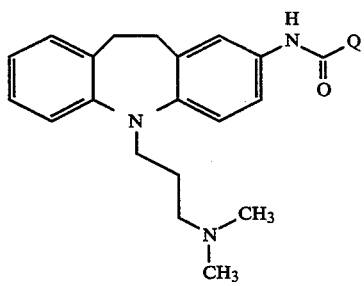

wherein

Q is a detectable moiety; and (b) measuring the amount of said labeled reagent in said reaction solution which either has or has not participated in a binding reaction with said antibodies as a function of the amount of amitriptyline in said test sample.

2. The method of claim 1 wherein said immunogenic carrier material is selected from the group consisting of bovine serum albumin, keyhole limpet hemocyanin, and thyroglobulin.

3. The method of claim 1 wherein said detectable moiety is selected from the group consisting of enzymes, chromophores, fluorescent molecules, chemiluminescent molecules, phosphorescent molecules, and luminescent molecules.

4. The method of claim 1 wherein said immunoassay method is a fluorescent polarization immunoassay wherein said detectable moiety of said labeled reagent is a fluorescent molecule which is capable of producing a detectable fluorescence polarization response to the presence of said antibodies for the quantification of amitriptyline in biological fluids.

5. The method of claim 4 wherein the amount of said labeled reagent is measured by (a) passing a plane of polarized light through said reaction solution to obtain a fluorescence polarization response and (b) detecting said fluorescence polarization response to said reaction solution as a function of amitriptyline in said test sample.

6. The method of claim 5 wherein (i) said fluorescent molecule is selected from the group consisting of aminomethyl-fluorescein, aminofluorescein, 5-fluoresceinyl, 6-fluoresceinyl, 5-carboxyfluorescein, 6-carboxyfluorescein, thioureafluorescein, and methoxytriazinolyl-aminofluorescein and (ii) said immunogenic carrier material is selected from the group consisting of bovine serum albumin, keyhole limpet hemocyanin, and thyroglobulin.

7. The method of claim 6 wherein (i) said antibodies are produced with an immunogen of the formula:

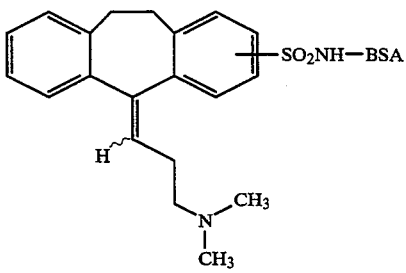

and (ii) said fluorescent molecule is 6-carboxyfluorescein.

8. An immunoassay method for the quantification of nortriptyline in a test sample, said method comprising the steps of:

(a) contacting said test sample with a labeled reagent and an antibody reagent to form a reaction solution therewith, said antibody reagent comprising antibodies which are capable of binding to nortriptyline, wherein (i) said antibodies are produced with an immunogen of the formula:

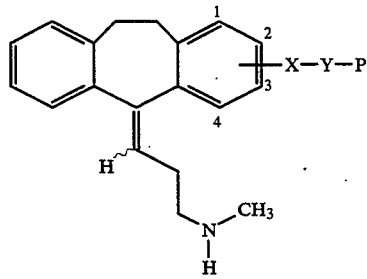

wherein

X is —SO$_2$—NH— linked to the aromatic ring in the 2 or 3 position, Y is a linking group comprising from 0 to 6 carbon atoms, and P is an immunogenic carrier material; and (ii) said labeled reagent for the specific quantification of nortriptyline is:

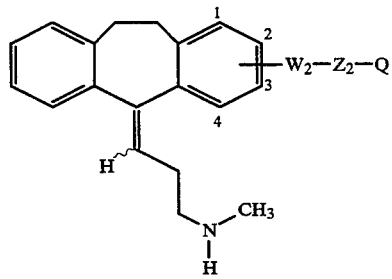

wherein

W$_2$ is —SO$_2$—NH— linked to the aromatic ring in the 2 or 3 position, Z$_2$ is —CH$_2$—CO— and Q is a detectable moiety; and (b) measuring the amount of said labeled reagent in said reaction solution which either has or has not participated in a binding reaction with said antibodies as a function of the amount of nortriptyline in said test sample.

9. The method of claim 8 wherein said immunogenic carrier material is selected from the group consisting of bovine serum albumin, keyhole limpet hemocyanin, and thyroglobulin.

10. The method of claim 8 wherein said detectable moiety is selected from the group consisting of enzymes, chromophores, fluorescent molecules, chemiluminescent molecules, phosphorescent molecules, and luminescent molecules.

11. The method of claim 8 wherein said immunoassay method is a fluorescent polarization immunoassay wherein said detectable moiety of said labeled reagent is a fluorescent molecule which is capable of producing a detectable fluorescence polarization response to the presence of said antibodies for the quantification of nortriptyline in biological fluids.

12. The method of claim 11 wherein the amount of said labeled reagent is measured by (a) passing a plane of polarized light through said reaction solution to obtain a fluorescence polarization response and (b) detecting said fluorescence polarization response to said reaction solution as a function of nortriptyline in said test sample.

13. The method of claim 12 wherein (i) said fluorescent molecule is selected from the group consisting of aminomethylfluorescein, aminofluorescein, 5-fluoresceinyl, 6-fluoresceinyl, 5-carboxyfluorescein, 6-carboxyfluorescein, thioureafluorescein, and methoxytriazinolyl-aminofluorescein and said immunogenic carrier material is selected from the group consisting of bovine serum albumin, keyhole limpet hemocyanin, and thyroglobulin.

14. The method of claim 13 wherein (i) said antibodies are produced with an immunogen of the formula:

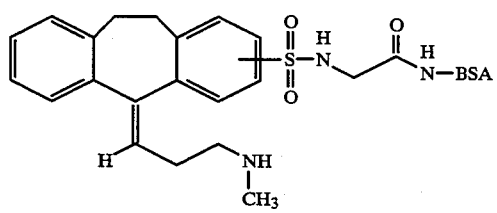

and (ii) said fluorescent molecule is aminomethylfluorescein.

15. A test kit for the quantification of amitriptyline in a test sample, said test kit comprising:
 (a) an antibody reagent comprising antibodies which are capable of binding to amitriptyline in a test sample, wherein said antibodies are produced with an immunogen of the formula:

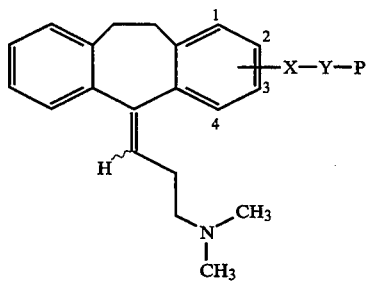

wherein
 X is —SO₂—NH— linked to the aromatic ring in the 2 or 3 position, Y is a linking group comprising from 0 to 6 carbon atoms, and P is an immunogenic carrier material; and
 (b) a labeled reagent which is recognizable by antibodies capable of binding amitriptyline in a test sample, wherein said labeled reagent is:

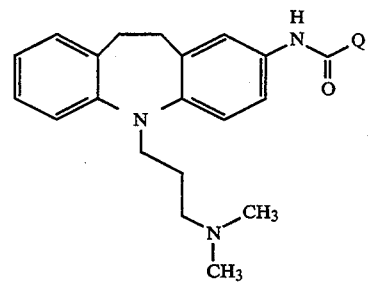

wherein Q is a fluorescent moiety.

16. The test kit of claim 15 wherein said immunogenic carrier material is selected from the group consisting of bovine serum albumin, keyhole limpet hemocyanin, and thyroglobulin.

17. The test kit of claim 15 wherein said fluorescent moiety is selected from the group consisting of aminomethyl-fluorescein, amino-fluorescein, 5-fluoresceinyl, 6-fluoresceinyl, 5-carboxyfluorescein, 6-carboxyfluorescein, thioureafluorescein, and methoxytriazinolyl-aminofluorescein.

18. The test kit of claim 15 wherein said antibody reagent is produced with an immunogen of the formula:

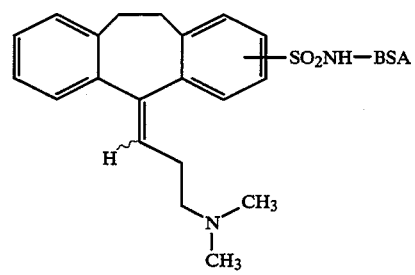

and
 said fluorescent moiety is 6-carboxyfluorescein.

19. A test kit for the quantification of nortriptyline in a test sample, said test kit comprising:
 (a) an antibody reagent comprising antibodies which are capable of binding to nortriptyline in a test sample, wherein said antibodies are produced with an immunogen of the formula:

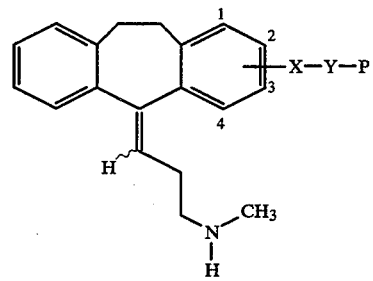

wherein X is —SO₂—NH— linked to the aromatic ring in the 2 or 3 position, Y is a linking group comprising from 0 to 6 carbon atoms, and P is an immunogenic carrier material; and (b) a labeled reagent which is recognizable by antibodies capable of binding nortriptyline in a test sample, wherein said labeled reagent is:

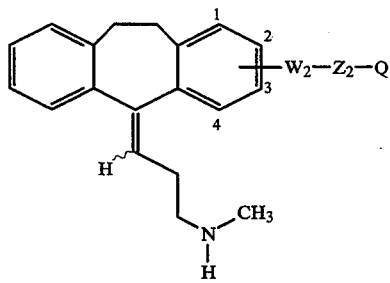

wherein
  $W_2$ is —$SO_2$—NH— linked to the aromatic ring in the 2 or 3 position, $Z_2$ is —$CH_2$—CO— and Q is a fluorescent moiety.

20. The test kit of claim 19 wherein said immunogenic carrier material is selected from the group consisting of bovine serum albumin keyhole limpet hemocyanin, and thyroglobulin.

21. The test kit of claim 19 wherein said fluorescent moiety is selected from the group consisting of aminomethylfluorescein, amino-fluorescein, 5-fluorescinyl, 6-fluorecsceinyl, 5-carboxyfluorescein, 6-carboxyfluorescein, thioureafluorescein, and methoxytriazinolyl-aminofluorescein.

22. The test kit of claim 19 wherein said antibody reagent is produced with an immunogen of the formula:

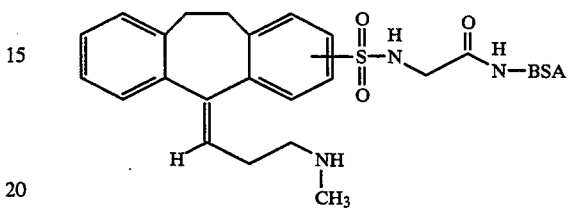

and
said fluorescent moiety is aminomethylfluorescein.

* * * * *